US011141195B2

(12) United States Patent
Ahluwalia et al.

(10) Patent No.: US 11,141,195 B2
(45) Date of Patent: Oct. 12, 2021

(54) UTERINE MANIPULATOR

(71) Applicants: Prabhat Kumar Ahluwalia, Little Falls, NY (US); Puja Ahluwalia, Little Falls, NY (US)

(72) Inventors: Prabhat Kumar Ahluwalia, Little Falls, NY (US); Puja Ahluwalia, Little Falls, NY (US)

( * ) Notice: Subject to any disclaimer, the term of this patent is extended or adjusted under 35 U.S.C. 154(b) by 796 days.

(21) Appl. No.: 15/632,425

(22) Filed: Jun. 26, 2017

(65) Prior Publication Data

US 2017/0333079 A1 Nov. 23, 2017

Related U.S. Application Data

(63) Continuation of application No. 15/073,358, filed on Mar. 17, 2016, now Pat. No. 9,717,525.

(60) Provisional application No. 62/134,359, filed on Mar. 17, 2015, provisional application No. 62/254,772, filed on Nov. 13, 2015.

(51) Int. Cl.

| | |
|---|---|
| ***A61B 17/42*** | (2006.01) |
| ***A61B 90/94*** | (2016.01) |
| ***A61B 17/00*** | (2006.01) |

(52) U.S. Cl.

CPC .......... *A61B 17/4241* (2013.01); *A61B 90/94* (2016.02); *A61B 2017/00429* (2013.01); *A61B 2017/00473* (2013.01)

(58) Field of Classification Search

CPC ...... A61B 2017/00433; A61B 17/4241; A61B 90/94; A61B 2017/00429; A61B 2017/00473; A61B 17/704

See application file for complete search history.

(56) References Cited

U.S. PATENT DOCUMENTS

| | | | | |
|---|---|---|---|---|
| 3,658,057 A * | 4/1972 | Cimber | A61F 6/08 | 128/836 |
| 4,775,362 A * | 10/1988 | Kronner | A61M 25/01 | 604/103.05 |
| 2011/0190579 A1* | 8/2011 | Ziarno | G06F 19/3418 | 600/109 |
| 2011/0259344 A1* | 10/2011 | Ahluwalia | A61B 17/42 | 128/834 |
| 2012/0143209 A1* | 6/2012 | Brecheen | A61B 17/4241 | 606/119 |
| 2013/0023896 A1* | 1/2013 | Quimby | A61B 17/4241 | 606/119 |
| 2014/0276916 A1* | 9/2014 | Ahluwalia | A61B 90/50 | 606/119 |

* cited by examiner

*Primary Examiner* — George J Ulsh
*Assistant Examiner* — Rachel S Highland
(74) *Attorney, Agent, or Firm* — Pierson IP, PLLC

(57) ABSTRACT

Embodiments disclose uterine manipulators, dye delivery systems and fornix delineators that address several issues, such as minimizing surgical error, minimizing loss of parts inside a patients, enabling easy manipulation of a patient's anatomy, securing and removing the device into and from the patient atraumatically, preventing loss of pnuemoperitoneum, and securing the device fastener and components efficiently and atraumatically. An embodiment includes a uterine manipulator having a fornix delineator, uterine shaft, outer tube, fastener, handle, inlet, tip, ring and connecting string, and/or occluder.

19 Claims, 24 Drawing Sheets

7w
7r
7a
7i
7o
7c
7s
7b
6
7e
7p
7c
7d
65
66

7d
7w
7c 7s
7b 8
7c
7i
7o
7a 7e
66
7r
65
7p
10
7o
7c
7a 7d
7a
7i
7r
7w
7c
7s
66
65

7e
7p
7b

FIGURE 11A
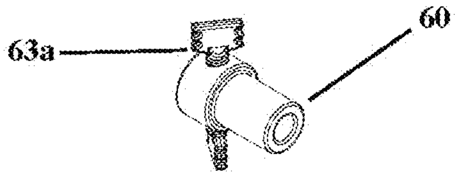
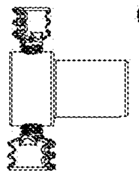
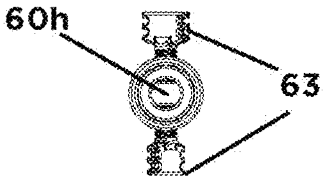
FIGURE 11B
FIGURE 11C
FIGURE 12A
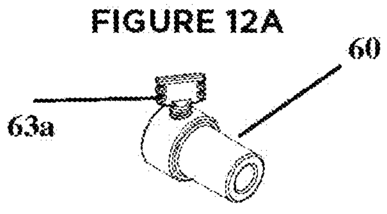
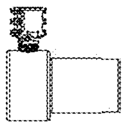
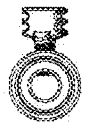
FIGURE 12B
FIGURE 12C

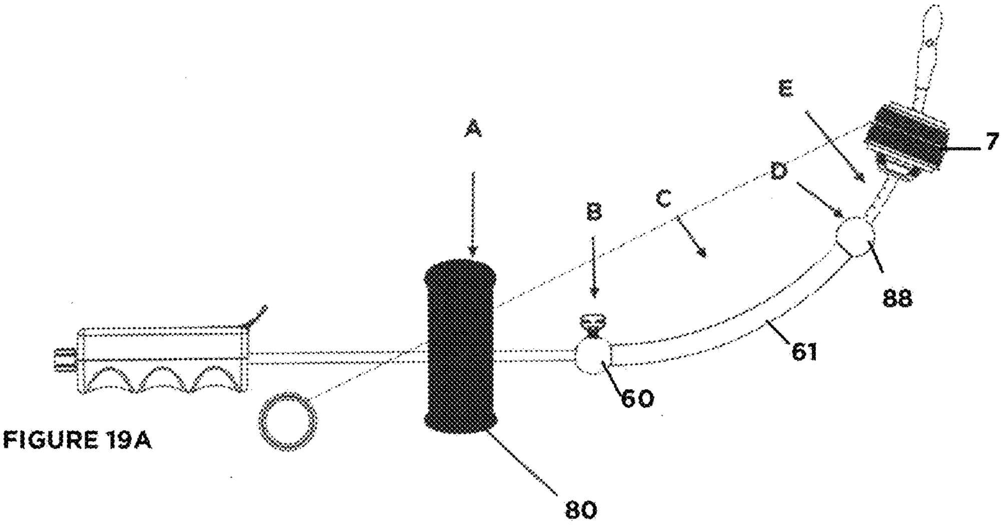
FIGURE 19A
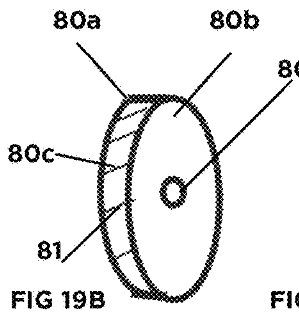
FIG 19B
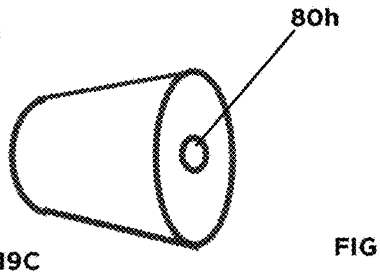
FIG 19C
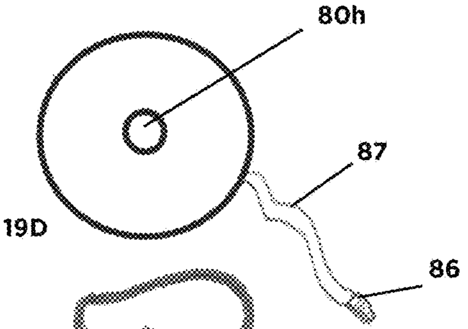
FIG 19D
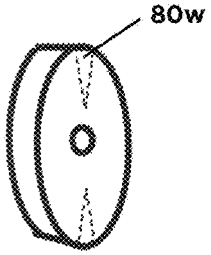
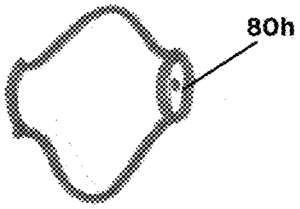
FIG 19F
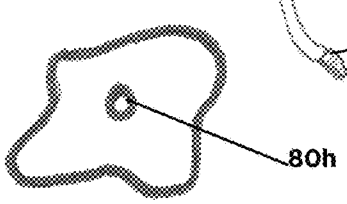
FIG 19G
FIG 19E

UTERINE MANIPULATOR

This application claims priority to U.S. Provisional Patent Applications 62/134,359 filed on Mar. 17, 2015 and 62/254,772 filed on Nov. 13, 2015, the content of which are hereby incorporated by reference.

BACKGROUND

U.S. patent application Ser. No. 13/091,517, entitled FORNIX MANIPULATOR and tiled on Apr. 21, 2011 ('517 application), shares a common inventor with the present application. The '517 application discloses a fornix manipulator including a collar and stabilizer to be attached to a uterine shaft. The fornix manipulator addresses several problems, including imprecise fornix delineation and deviation; vaginal shortening; abdominal deflation; blocked cervical access; unnecessary tissue damage from blind cervical retrieval, device insertion and retrieval, and lack of a platform for organ dissection.

U.S. patent application Ser. No. 14/204,766, entitled UTERINE MANIPULATOR and filed on Mar. 11, 2014 ('766 application), shares a common inventor with the present application. The 766' addresses several problems and injuries may result when using conventional devices, known as uterine manipulators, to manipulate the fornix. These problems include imprecise fornix delineation and deviation; vaginal shortening; abdominal deflation and injury from blind cervical retrieval; device insertion and retrieval, and lack of a platform while dissecting vital organs away from the fornix and vaginal wall.

BRIEF DESCRIPTION OF DRAWINGS

The accompanying drawings are included to provide a further understanding of the general inventive concept and are incorporated in and constitute a part of this specification. The drawings illustrate exemplary embodiments of the general inventive concept and, together with the description, serve to explain principles of the general inventive concept. Features and advantages of embodiments of the present invention will become apparent from the appended claims, the following detailed description of one or more example embodiments, and the corresponding FIGURES:

FIGS. 11A-C show perspective, side and frontal views of an embodiment of a fastener or locking portion configured to receive two screws with crevices.

FIGS. 12A-C show perspective, side and frontal views of an embodiment of a fastener or locking portion configured to receive one screw with crevices.

FIG. 19A shows an embodiment of a uterine manipulator with an occluder.

FIG. 19B shows an embodiment of an occluder shaped as a disk.

FIG. 19C shows an embodiment of an occluder shaped as a cylinder or a of cone.

FIG. 19D shows an embodiment of a balloon occluder.

FIG. 19E shows an embodiment of an occluder shaped as a disk with wedges or crevices FIG. 19F-19G show embodiments of an occluder.

DETAILED DESCRIPTION

Preferred embodiments of the general inventive concept will be described below in more detail with reference to the accompanying drawings. These embodiments are provided so that this disclosure will be thorough and complete, and will convey the scope of the general inventive concept to those skilled in the art. The embodiments of the general inventive concept may, however, be embodied in different forms and should not be constructed as limited to the embodiments set forth herein. Although numerous specific details are set forth, embodiments of the invention may be practiced without these specific details. "An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner. Like numbers refer to like elements throughout. Well-known structures and techniques have not been shown in detail to avoid obscuring an understanding of this description.

An embodiment of the invention includes an improvement to uterine manipulators and dye delivery systems that addresses several issues, such as minimizing surgical error, minimizing loss of parts inside a patients, enabling easy manipulation of a patient's anatomy, securing the components of a device with a fastener atraumatically, preventing loss of pnuemoperitoneum, and securing the device within the patient for precise delineation. Embodiments are not limited to addressing these issues, and other benefits, features, and/or utilities may be apparent to one of ordinary skill in the art. An embodiment of a uterine manipulator may include a fornix delineator, uterine shaft, outer tube, fastener, handle, inlet, tip, ring and connecting string, and/or occluder. However, embodiments may not include all components; for example uterine manipulators intended for general manipulation without colpotomy may lack a fornix delineator (such as a collar and stabilizer), ring, string and occluder. In addition, alternative components may be substituted; for example a collar and/or stabilizer may be substituted by an alternative fornix delineator, such as cup 8 or pronged cup 6. Similarly, a variety of fasteners may be employed, some of which have been described and are incorporated by reference by the 766' application.

Figure 1A:
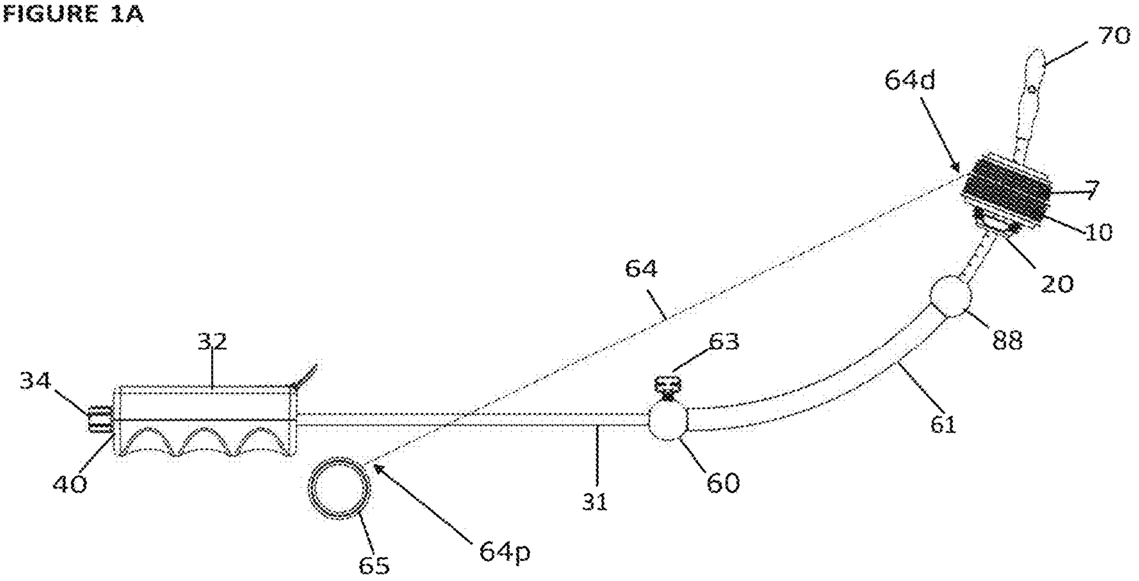
FIGS. 1A and 1B show a side and perspective view respectively of an embodiment of a uterine manipulator with a retrieval ring and creviced screw.
Figure 1B:
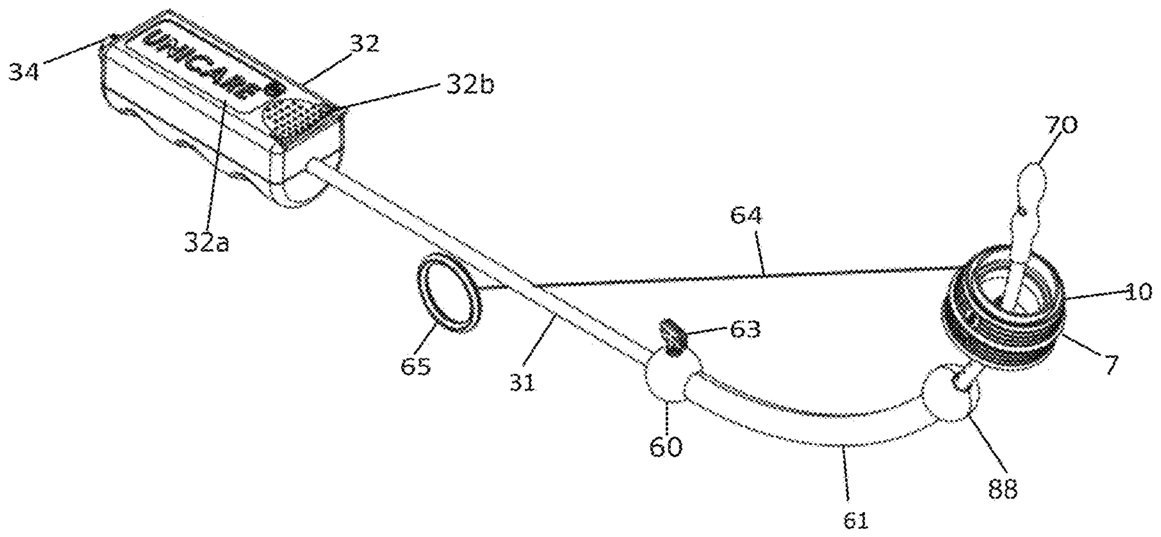

FIGS. 1A and 1B show a side and perspective view respectively of an embodiment of a uterine manipulator 30, including a fornix delineator 7 (in this embodiment, comprised of collar 10 and stabilizer 20), tip 70, handle 32, inlet 40, cap 34, uterine shaft 31, outer tube 61 (in this embodiment, including a distal ball 88), and a fastener or locking portion 60 (in this embodiment, comprised of a ball 60*b* and thumb screw 63), string 64, and ring 65. Embodiments may also include an occluder, such as made from foam, sponge or balloon, as shown in FIGS. 19 & 20.

In this embodiment, the rounded distal ball 88, a rounded fastener or locking portion 60, and ring 65 for retrieval attached to the fornix delineator ensures the fornix delineator is not lost inside the patient's abdominal activity after surgery, allows for quick device retrieval, and ensures the fornix delineator and/or device is least atraumatic upon insertion and retrieval to the patient. In addition, the screw 63 with crevices 63*a* allows definition during colptomy and prevents loss of pnuemoperitoneum. Handle 32 is designed for ergonomic use of the device.

FIGS. 1A and 1B show a side and perspective view of an embodiment of a handle 32. The handle may include a logo 32*a* and thumb rest 32*b* with an array dotted protrusions for a grip. In addition, the handle may have an internal structure configured for receiving a shaft 31, such as an internal tube 32*c*. The handle 31 may also have the inlet 40 integrated into the proximal end and/or integrated with the internal handle tube 32*c*.

Figure 2:
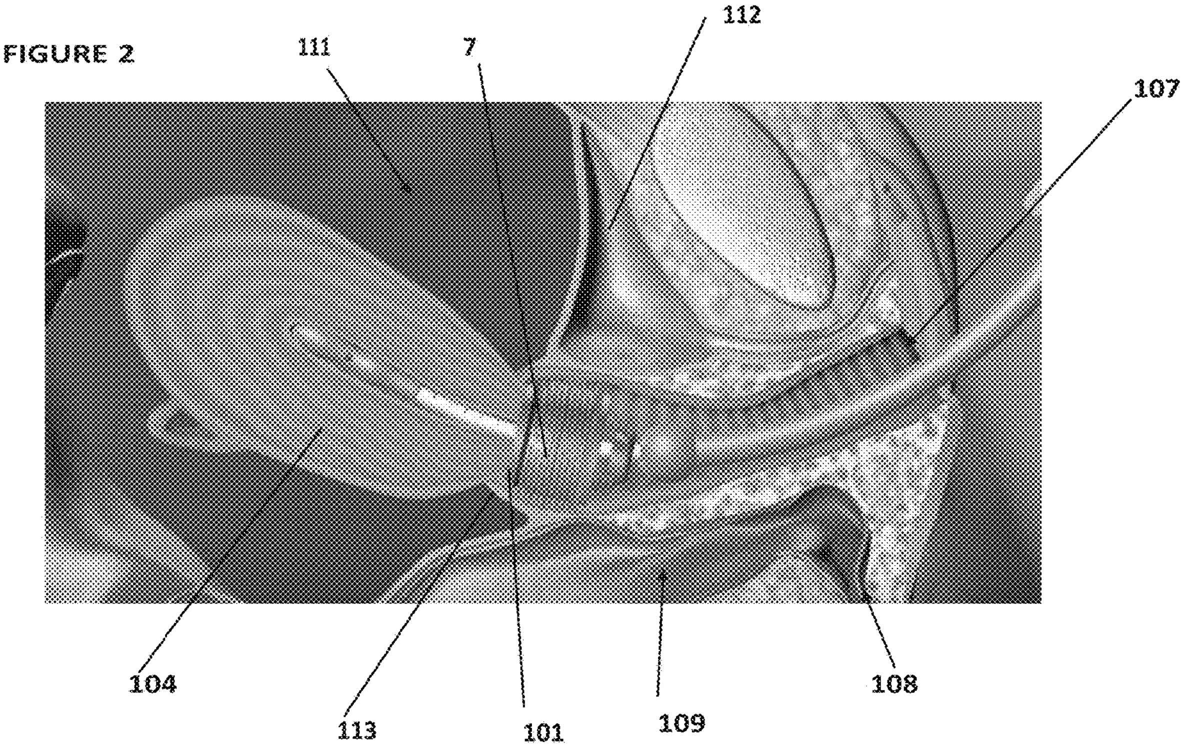
FIG. 2 shows a sagittal cross-section of an embodiment of a female pelvis with uterine manipulator.

FIG. 2 shows a sagittal cross-section of a female pelvis with uterine manipulator 30. The cervix opens into the uterus 104. On one side of the vagina 107, toward the front of the body, is a bladder 112. On another side of the vagina 107, toward the rear of the body, is the rectum 109 and the anus 108, which opens from the rectum 109 to outside the body. Surgeons may access the uterus 104 and other organs from the abdominal cavity 111. The fornix is a cylindrical ring of tissue encircling the cervix 104*a* and lower uterus. The lowest cylindrical ring is the intra-vaginal fornix 101, which encircles the cervix and is visible from the vaginal canal. The upper-most cylindrical ring of the fornix is the intra-abdominal fornix 113. When viewed from the abdomen, the anterior half of the intra-abdominal fornix 113 may be visible, but it is neither demarcated nor obvious to the human eye. The ring of the intra-abdominal fornix 113 passes between the uterus 104 and rectum 109, and also passes between the uterus 104 and bladder 112, as indicated by FIG. 2.

FIGS. 1A and 1B show a ring 65 configured to connect to the proximal end 64*p* of a string or string 64 (hereinafter "string 64"), where the distal end 64*d* of string 64 is coupled to a fornix delineator 7, which in this embodiment is collar 10. Ring 65 and string 64 may also be configured to couple to other embodiments of fornix delineators, such as a cup 8 (shown in FIG. 3G-3I), pronged cup 6 (shown in FIG. 3D-3F), collars 10 and stabilizers 20 previously described in the 517' and 766' applications, in addition to any cervical delineator, cup, collar, cervical ring or medical device configured to define or delineate the vaginal fornices or surround the cervix.

Figure 3A:
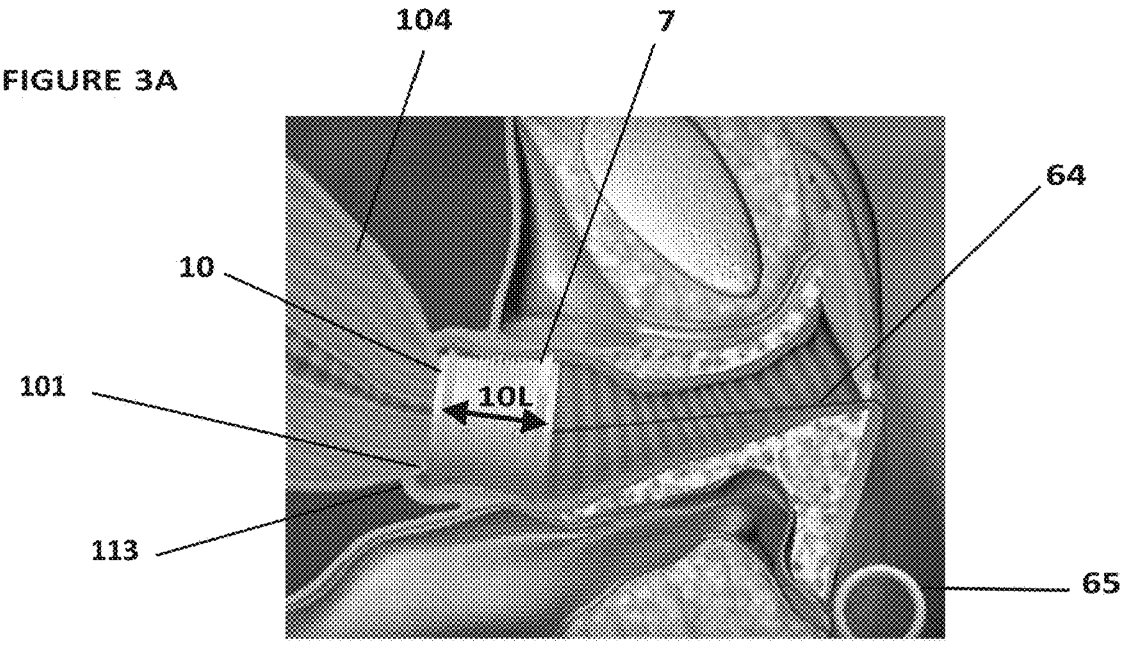
FIGS. 3A-3C show an embodiment of an operation of removal of a fornix manipulator from the vaginal canal via pulling a ring and string coupled to the fornix delineator.
Figure 3B:
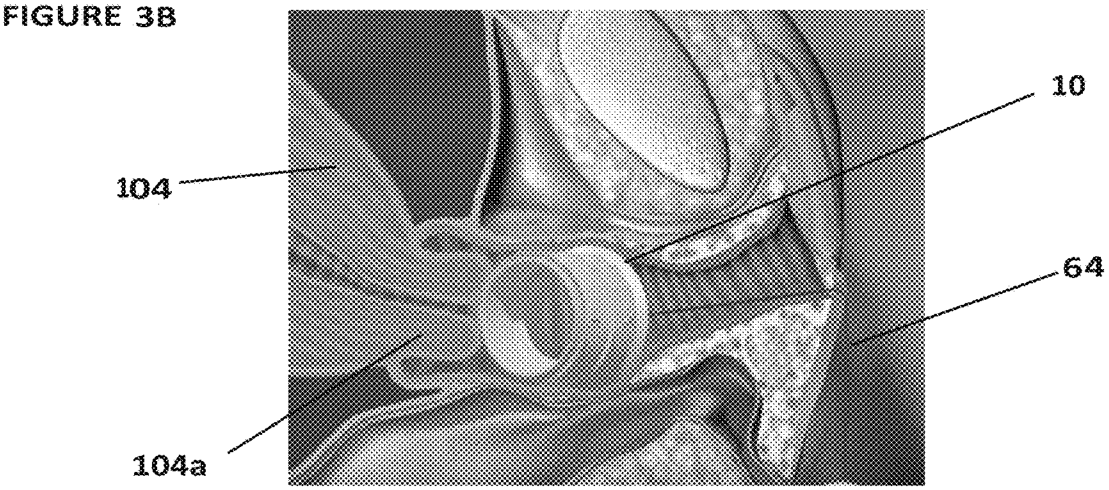
Figure 3C:
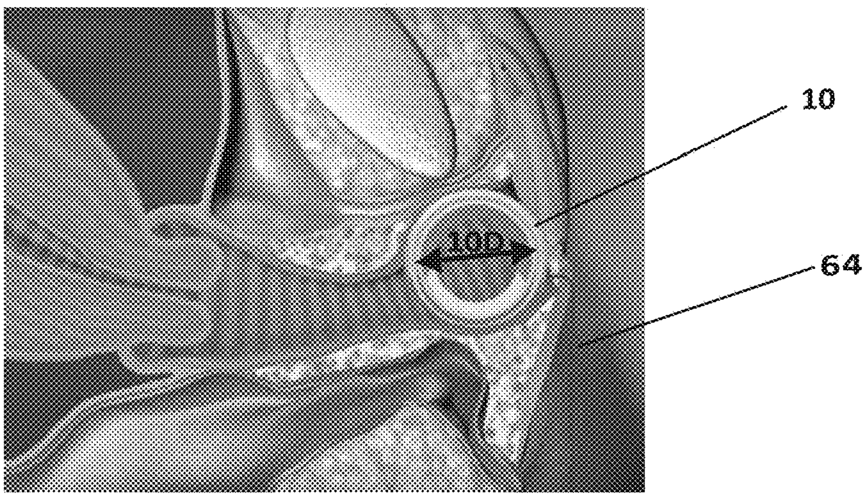
Figures 3D, 3E, 3F, 3G, 3H, 3I, 3J, 3K:
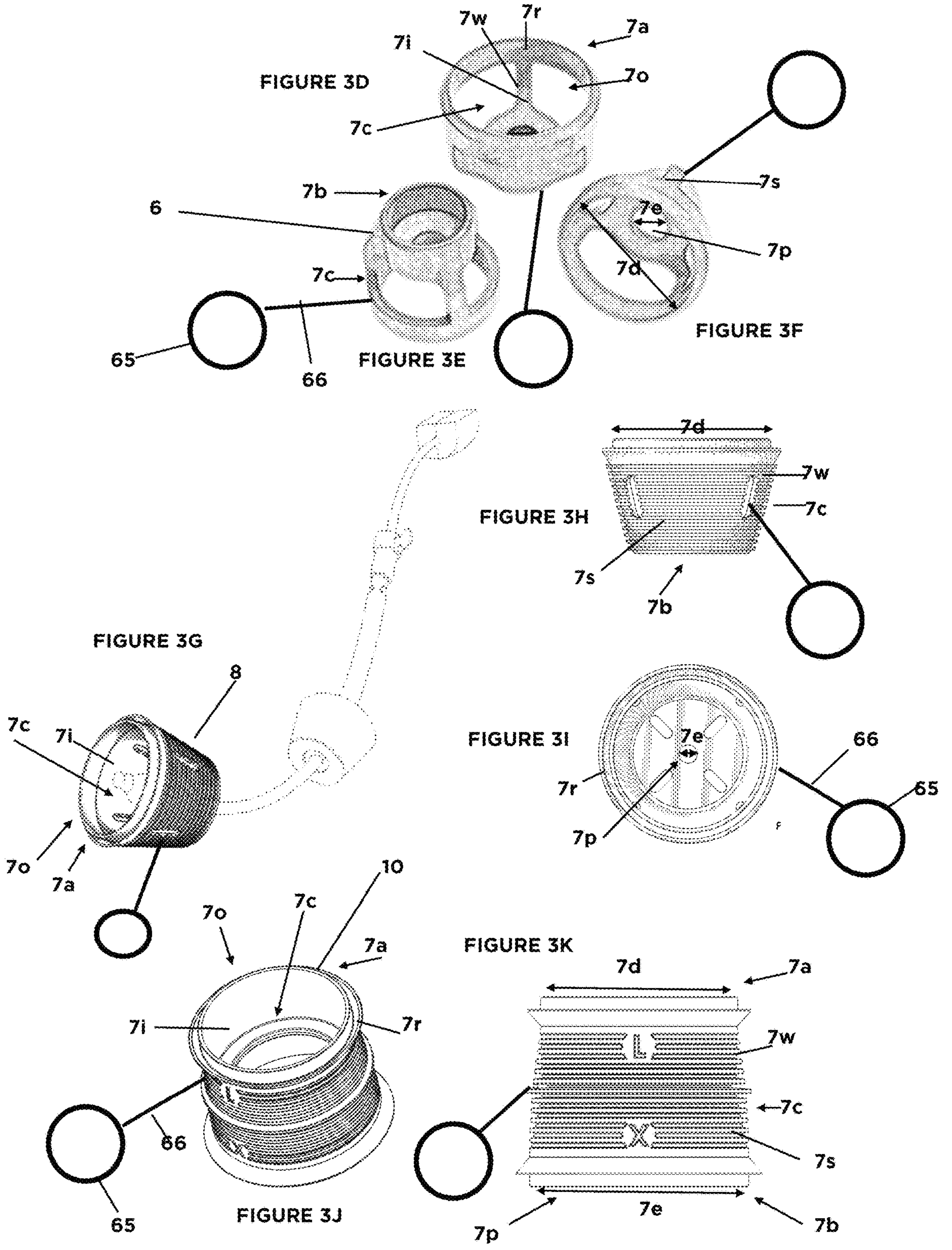
FIGS. 3D-3F show perspective views of an embodiment of a fornix delineator, that is a pronged cup coupled to a string and retrieval ring.
FIG. 3G-3I shows a side, perspective, and top views respectively of an embodiment of a fornix delineator that is a cup coupled to a string and retrieval ring.
FIG. 3J-3K shows a perspective and side views respectively of an embodiment of a fornix delineator that is a collar 10 coupled to a string and retrieval ring.

For example, FIGS. 3D-3F show perspective views of an embodiment of a fornix delineator, pronged cup 6, which may couple to a string 64 and ring 65 for retrieval from the vaginal canal. FIG. 3G-3I shows a side, perspective, and top views of an embodiment of a fornix delineator, cup 8, which may also couple to a ring 65 and string 64 for retrieval from the vaginal canal. In this embodiment, cup 8 is shown to have a ribbed surface, however in other embodiments it has a smooth surface. FIG. 3J-3K shows a perspective and side views respectively of an embodiment of a fornix delineator, collar 10, which may also couple to a ring 65 and string 64 for retrieval from the vaginal canal.

A fornix delineator 7 may have a first end 7*a* comprising a first opening 7*o*, having a first diameter 7*d*, surrounded by a first rim 7*r*. First rim 7*r* may be adapted to contact and define or delineate the vaginal fornices, or surround the cervix. Fornix delineator 7 may have a second end 7*b*, opposite the first end, which may have second opening 7*p* with a second diameter 7*e* adapted. Second opening 7*p* may be configured to receive a shaft or a tip for insertion into the cervical os. Fornix delineator 7 may have a third portion 7*c* consisting of one or more prongs, wall, or wall with windows 7*w* coupling the first end 7*a* to the second end 7*b*. Third portion 7*c* may have inner surface 7*i* adapted to contact a cervix and an outer surface 7*s* adapted to contact a vaginal wall. The first end 7*a*, second end 7*b* and prongs, wall, or wall with windows (hereinafter "wall 7*w*") may define a cylindrical, conical or partially conical inner cavity 7*c*. Inner cavity 7*c* may be configured to receive a cervix. Additional features or specific geometries may be modified unique to the particular fornix delineator, shaft, or uterine manipulator to which it is attached. The openings and rims may be rounded, for example.

For the sake of brevity, figures illustrate an application of a ring 65 and string 64 to a fornix delineator 7 in the form of a collar 10. However, in embodiments, collar 10 may be substituted by alternative fornix delineators, such as cups 8, pronged cups 6, alternative collars 10, stabilizers 20, and other market and readily available fornix delineators. Thus, throughout this specification, any discussion or description of the collar 10 coupled to a ring 65 and strap 64 also applies to embodiments wherein the collar 10 is substituted by alternative fornix delineators, such as cups 8, pronged cups 6 alternative collars 10, stabilizers 20, and other market and readily available fornix delineators. A limited but not exhaustive of examples of such embodiments of fornix delineators are shown in FIGS. 3D-3H, in addition to collars 10 and stabilizers 20 currently described and previously described in the 517' and 766' applications.

Ring 65 coupled to string 64 serves a critical function of preventing loss of the fornix delineator (collar 10, cup 8, or other embodiment) inside the patient after colopotomy. This may occur if the fornix delineator is a removable part, or if it is not removable; as reported by the Food and Drug Administration, loss of a fornix delineator or cup is not an infrequent occurrence, even in devices where fornix delineator is not removable but fixed into position on a uterine manipulator. Loss of the fornix delineator typically results when the fornix delineator has a diameter larger than the diameter of the vaginal introitus and therefore slides or is pushed off the manipulator upon retrieval of the medical device from the vaginal canal; the vaginal introitus may not allow passage of the fornix delineator, and responsive to being pulled against the vaginal introitous, the fornix delineator may slide of the manipulator or medical device and fall into the vaginal and into the patient.

Ring 65 provides an additional weight to the otherwise light-weight string 64, which may be a thin suture, which is easily lost within in the vaginal canal or may blend in the draping in an operating room. Ring 65 keeps the distal end 64*d* of the string outside of the patient, and allows the surgeon to quickly identify the location of the string, and pull the string for retrieval of the fornix delineator. The ring enables a surgeon to grasp or pull string 64 to facilitate atraumatic and efficient retrieval of the fornix delineator. Also, during removal, the physician is able to hold the ring to prevent loss of the fornix delineator during removal, which is when delineators are typically lost.

String 64 may be comprised of a string, suture material or any other material which facilitates coupling of the ring to a cup or collar. In addition, the ring may be circular, oval, square, polygonal, mixed shape or any other shape which enables a grasping by a practitioner. In embodiments, ring 65 may be a solid weight without a center hole, graspable by hand. The weight may or may not include an eyelet or protrusion for receiving, coupling, or tying string 64. In Addition, the ring may be any size, and in particular a size significantly larger than the vaginal introitus (e.g., greater than 1 inch) to prevent the ring from sliding into the vaginal canal. Strap 64 may also have a length sufficient to ensure that the ring 65 hangs out side the vaginal canal (e.g., 5 inches or more). In embodiments, ring 65 may be integral with string 64 or separate components. String 64 may be elastic or inelastic. Distal end 64*d* of string 64 may be attached to an eyelet on a fornix delineator or simply tied around any base portion, arms, holes, wall 7*w*, inner surface 7*i*, outer surface 7*s*, rims, or any other portion of the fornix delineator (e.g., collar 10, cup 8 or pronged cup 6).

Ring 65 is configured to couple to a string 64 and hang outside of the vagina 107. Ring 65 enables a practitioner to pull or retrieve the fornix delineator atraumatically. As shown in FIGS. 3A-3C, responsive to pulling ring 65, the practitioner pulls string 64, which in turn pulls collar 10 off the cervix and/or vaginal fornixes. As the collar is pulled from the distal to the proximal end of the vaginal canal, the collar rotates to it's most atraumatic orientation for retrieval from the vaginal canal. This may be critical to keep the vaginal introitus intact. In other words, pulling ring 65 enables the collar to rotate to its most atraumatic orientation and be removed sideways. While being removed sideways, the collar 10's minimal length 10L exits the vaginal introitus rather than in its maximal diameter 10D orientation. Collar Length 10L is less than diameter 10*d* so minimizes impact.

FIGS. 3A-3C shows an operation of removal of the ring. FIG. 3A, shows a collar 10 positioned surrounding the cervix 104*a* and pressing against intra-abdominal fornix 113 and intra-vaginal fornix 101. As shown FIG. 3B, the practitioner pulls ring 65 from a position that is remote from the vaginal canal, which thereby pulls string 64, which in turns pulls collar 10 off the cervix 104*a*. Collar 10 rotates to an atraumatic orientation. In this embodiment, as shown in FIG. 3C, the collar 10 is shown to rotate 90 degrees within the vaginal canal. At this atraumatic orientation shown in FIG. 3C, the collar length 10L exists the vaginal canal, rather than the larger diameter 10D, responsive to pulling on the ring 65 further.

In other embodiments, wherein a collar is substituted by another embodiment of a fornix delineator, such as cup 8, the device may rotate less than 90 degrees to an atraumatic orientation. Depending on the geometry collar, the collar itself may rotate less than 90 degrees.

For a fornix delineator (e.g., collar 10, cup 8, pronged cup 6) that is being retrieved by ring 65 and string 64, the resistance of the vaginal introitus to the fornix delineator being removed via the pull force of the ring 65 forces the fornix delineator to rotate to a more atraumatic orientation before exiting the vaginal canal. In addition, the ring 65 has the benefit of easing surgical practice so the surgeon may avoid blinding grasping or fish for the string, which may easily blend in color with draping, be lost within draping, or be lost within the vaginal canal. In addition, ring 65 prevents loss of the fornix delineator into the patient.

Fornix delineator 7 may be detachable from the uterine manipulator, and the ring and string 64 may facilitate removal of the fornix delineator separate from or together with the manipulator. In other embodiments, fornix delineator may also be coupled or affixed onto the uterine manipulator, so removal of the delineator via pulling the ring also leads to removal of the manipulator or medical device. For example, for the embodiment shown in FIG. 3G, the ring and string 64 facilitate removal of cup 8 and the attached uterine manipulator.

Ring 65 is critical to the removal of the fornix delineator in an atraumatic orientation as it permits the surgeon to grasp string 64 with ease in an operating context where time is critical. The ring prevents repeated slippage of string 64 from the surgeon's fingers or clamps and provides sufficient grip to permit application of sufficient pull force to pull the fornix delineator off the cervix and rotate within the vaginal canal. In addition, ring 65 prevents loss of parts of the fornix delineator into patient, by being a weight that hangs outside the vaginal canal.

The ring 65 and string 64 retrieval technology is unique for assisting removal though a narrow vaginal canal, which requires atraumatic removal of devices. Accordingly, the ring and string 64 may be affixed to any cervical, vaginal or uterine cup, diaphragm, collar or vaginal or uterine manipulator device.

Figure 4A:
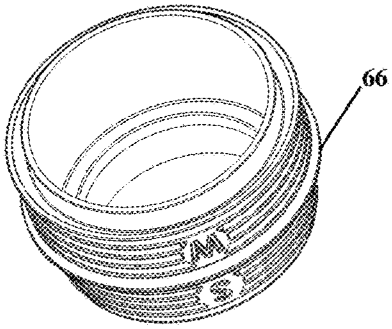
FIGS. 4A-4B show a perspective and side view of an embodiment of a fornix delineators with size markings, a ridge, and an eyelet.
Figure 4B:
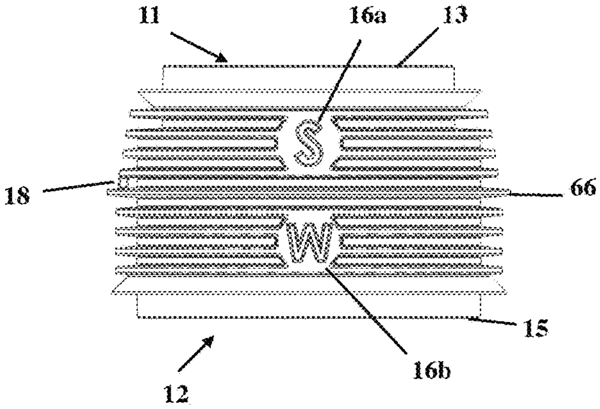
Figure 5A:
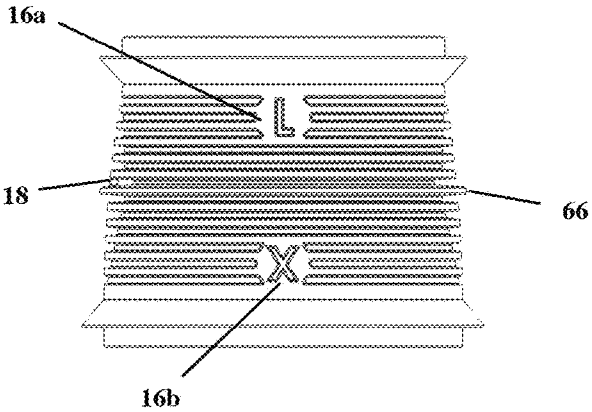
FIGS. 5A-5B show a perspective and side view of an embodiment of a fornix delineators with size markings, a ridge, and an eyelet.
Figure 5B:
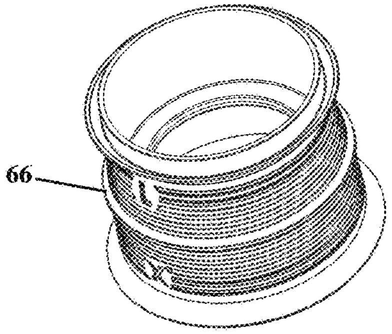

FIGS. 4 and 5 show embodiments of collars 10 wherein size markings 16 of the collar are indicated between the either end of the collar to enable easy identification of collar size and appropriate use of the right sized collar on the particular cervix and/or vaginal fornixes, given variations in cervical and vaginal anatomy. FIG. 4A shows a perspective view of an embodiment of a collar 10, and FIG. 4B is a side-view. In embodiments wherein the collar 10 is a dual-use or dual-rimmed collar with a first end 11 and second end 12 of different diameters, two size markings 16*a* and 16*b* may be positioned on the collar to indicate the size of the particular end, in the embodiments shown, a first size marking 16*a* is positioned between the collar's first end 11 and the midpoint, and a second size marking 16*b* is positioned between the collar's second end 12 and midpoint.

Any sizing symbol may be used (letters, numbers, symbols, etc.) such as the letters "S", "M", "L" and "X" as shown in FIGS. 19 and 20. The size marking may be oriented so that the appropriate letter is facing up, depending on the orientation of the collar. For example the size "M" may appear as a "W" if that end of the collar is not being utilized. But when orientated for placement around a cervix, the "W" appears as an "M".

Figure 6:
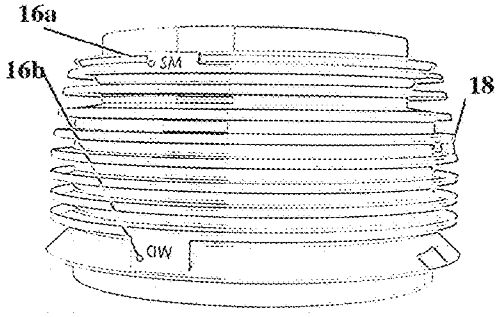
FIG. 6 shows a perspective view of an embodiment of a fornix delineators with size markings and an eyelet.

Size marking 16 may be positioned on any location of the collar 10 to enable easy identification of collar size. For example, size marking 16 may be positioned on collar rim 13 or collar rim 15 or adjacent to a collar rim. For example, FIG. 6 shows an embodiment where size marking 16 is positioned along or adjacent to collar rim 13 or 15. FIG. 6 also shows an alternative embodiment of size markers 16*a* and 16*b*. In another embodiment, the size markers are written along a rim, such as the colpotomy rim. In another embodiment, the product's name is written along the rim. For example, the letters "UNICARE" may be etched onto one or more of the collar's rim.

More or less than 4 sizes may be shown. For example, each collar may only include a single size marking. Size markings may be circular, squared, or any other mixed, polygonal or trapezoidal shape. In another embodiment, only one size may be indicated.

FIGS. 4 & 5 also show a distended ridge, ring, or shelf (hereinafter "ridge") 66 located in or around the midpoint of the fornix delineator 7, which in this embodiment is a collar 10. For the sake of brevity, FIGS. 4 & 5 show an embodiment of a fornix delineator that is a collar 10, however a ridge 66 may also be applied to any embodiment of an alternative fornix delineator, such as a cup 8, pronged cup 6, in addition to collars 10 and stabilizers 20 currently described and previously described in the 517' and 766' applications, and other market and readily available fornix delineators.

This ridge extends beyond the fornix delineator wall and is visible laparoscopically or internally and visualizes the midpoint of the fornix delineator to the surgeon. This ridge enables the surgeon to know the exact placement of the fornix delineator, and prevents the surgeon from dissecting vaginal tissue instead of the vaginal fornix and therefore also minimizes injuries to nearby vital organs such as ureters, bladder and bowel. Ridge 66 may be single ridge or multiple ridges 66 positioned along the fornix delineator, and may be evenly or unevenly spaced. A series of ridges 66 may enable a practitioner to gauge to distance or depth of insertion of the delineator, and the length of the distended vaginal wall and/or cervix intra-abdominally to know the exact position of the delineator.

The ridge may be 0.5-20 mm extending from fornix delineator wall. In this particular embodiment, it's 2-10 mm extending from the fornix delineator wall. The ridge(s) may be angled or straight up. Ridge 66 may have the largest diameter of any of the ridges along the outer surface of the fornix delineator. As such, ridge 66 projects past each of the other ridges. In embodiments, the distance between the top and bottom surfaces of the fornix delineator may be equal.

Ridge 66 may be uniform in wall thickness and may have a smooth surface or may have a regular or irregular patterned surface. For example the surface may be zigzagged, corrugated, or be comprised of a series of evenly spaced or unevenly protrusions to differentiate it's rim surface from the rim of the fornix delineator during colpotomy.

Figure 7A:
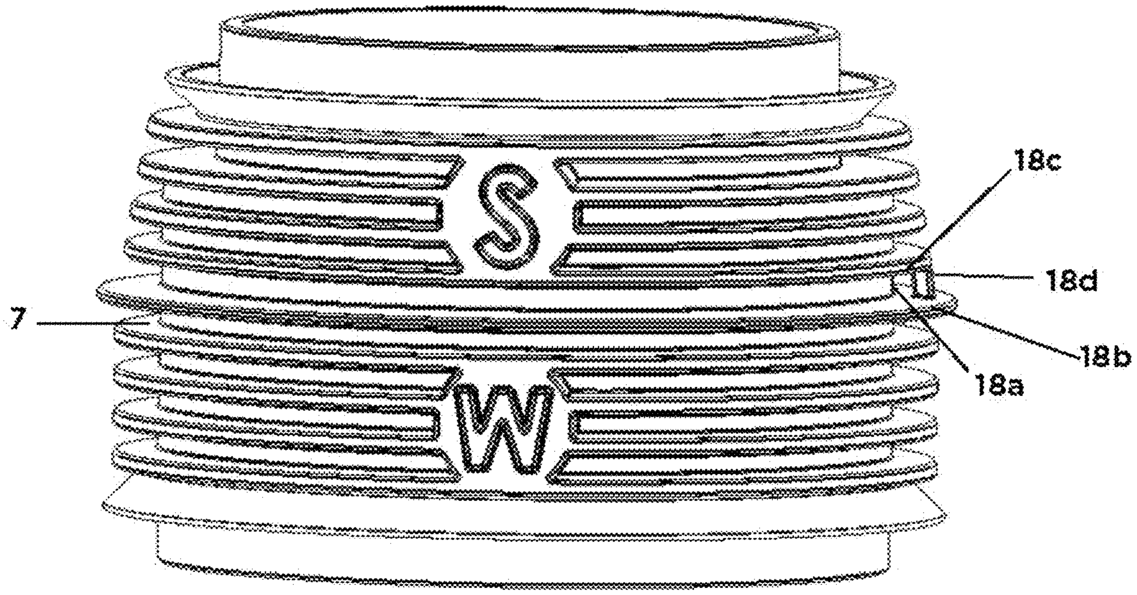
FIGS. 7A-7B show a perspective views of an embodiment of a fornix delineator with size markings, a ridge, and an eyelet.
Figure 7B:
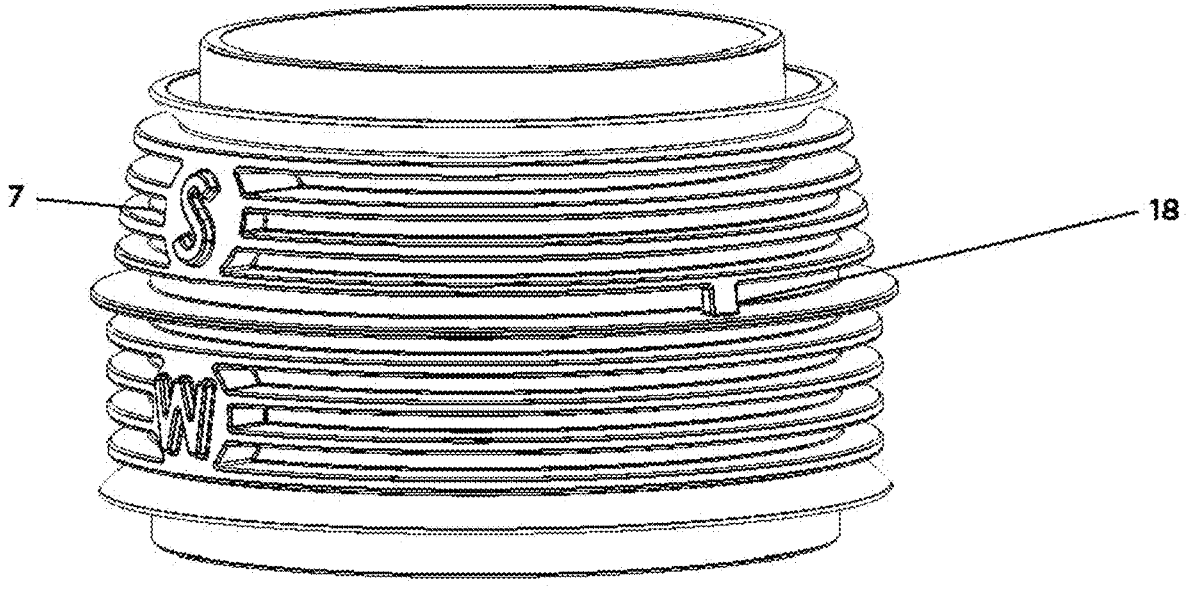
Figure 8B:
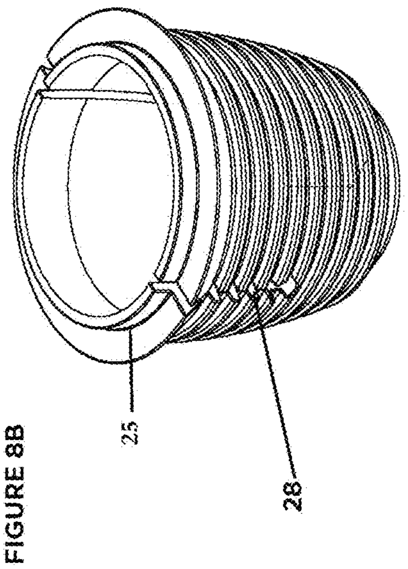
FIG. 8A-8D shows an embodiment of a stabilizer wherein the stabilizer has a slit.
Figure 8A:
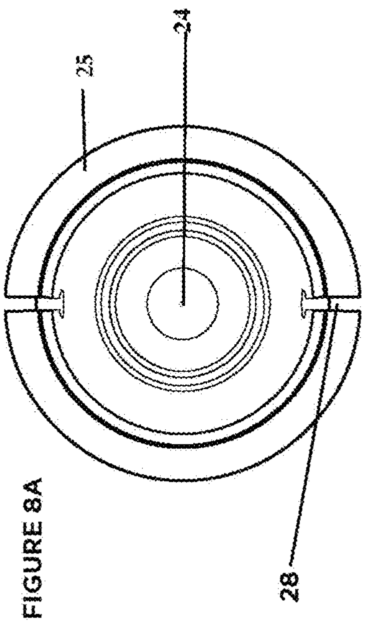
Figure 8C:
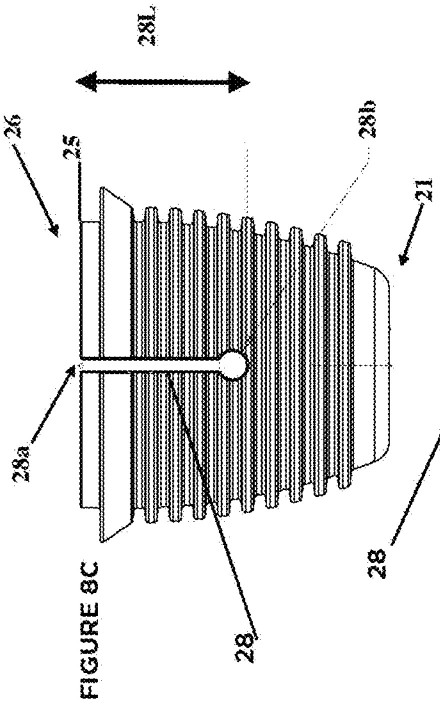
Figure 8D:
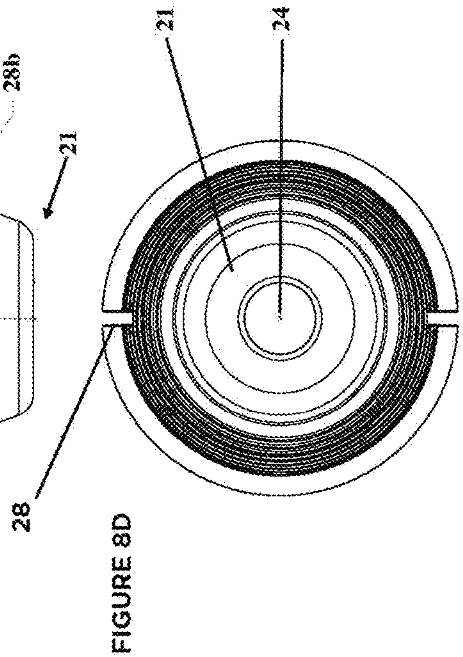

FIGS. 7A & 7B show that a fornix delineator may also contain a notch, aperture, or eyelet (hereinafter "eyelet") 18 for looping, threading, coupling or affixing a suture, string 64. For the sake of brevity, FIGS. 7A & 7B show an embodiment of a fornix delineator that is a collar 10, however an eyelet may also be applied to any embodiment of an alternative fornix delineator, such as a cup 8, pronged cup 6, in addition to collars 10 and stabilizers 20 currently described and previously described in the 517' and 766' applications, and other market and readily available fornix delineators.

In embodiments, eyelet 18 may be positioned at a position that is at midway position or substantially midway position along the height of the fornix delineator. In embodiments, eyelet may also be positioned on or adjacent to the delineator's first end 7*a*, second end 7*b*, third portion 7*c*, wall 7*w*, inner surface 7*i*, or outer surface 7*s*.

As shown in FIG. 7A, the eyelet may be comprised of a wall 18*a* as a first side surface, a first rib as a bottom surface 18*b*, an opposite rib as a top surface 18*c*, and material between two ribs or ridges as a second side surface 18*d*. Alternatively, the eyelet may form part of any rib, inner or outer sidewall, rim or any portion of the fornix delineator. The eyelet may protrude from the device or be integral or recessed within the device. Accordingly, eyelet 18 may be positioned between two ribs of fornix delineator 7, and horizontally offset from the fornix delineator, such that a distance from a center of the fornix delineator to the fornix delineator wall 18*a* is less than a distance from the center of the fornix delineator to eyelet 18.

Alternate embodies of an eyelet may be utilized. For example, a simple protrusion may extend from the fornix delineator with a hole to receive string 64. Alternatively, the hole may be integrated within the fornix delineator.

FIG. 8A-8D shows an embodiment of a stabilizer 20 wherein the stabilizer has a slit 28. FIGS. 8A, 8B, 8C and 8D are a top, perspective, side, and bottom views respectively of the embodiment. Slit 28 permits passage of a cervical stitch through the stabilizer so that the stitch may pass outside of the vaginal canal and affix to a thumbscrew, tenaculum, or another portion of the medical device or hang freely for manual manipulation. Affixing a stitch to the cervix and attaching it to the a portion of the medical device, such as a thumbscrew, enables a practitioner to apply more pressure of the manipulator against the vaginal fornixes, leading to better delineation. The slit is an advantage over existing art as it minimizes the loss of pnuemoperitoneum when a colpotomy incision is made around the vaginal fornices, in contrast to windows which may permit leak of CO2 or loss of pnuemoperitoneum during a colpotomy incision on the vaginal fornixes.

In some embodiments, a single slit 28 is on the stabilizer. In other embodiments, two or more slits 28 may be positioned on the stabilizer, for example on the opposite sides of the stabilizer as shown in FIG. 8. The slits 28 may extend a length 28L from the rim 25 of the stabilizer towards the base portion 21 of the stabilizer. The slit may extend most or a partial length, comprised of an open end 28*a* and a closed end 28*b*. In the embodiment in FIG. 32*a*, the slits extend approximately half the height of the stabilizer. The first open end 28*a* may have first width, and the closed end 28*b* may have with second width. First open end 28*a* may include planar sidewalls, wherein the sidewalls are in parallel with each other. The closed end 28*b* may have variable widths that increase and decrease to form a round, closed end, as shown in FIG. 8. The maximum length of the second portion of the slit may be longer than the width of the first portion of the slit.

In other embodiments, the open end 28*a* and a closed end 28*b* may be identical in width and form a rectangular slit. In other embodiments, the first width may narrow to a point in the closed end 28*b*, forming a triangular slit. The slit may be any polygonal, oval, square, rectangular or mixed shape extending from the upper surface of the stabilizer toward the bottom surface of the stabilizer.

In embodiments, the first width may be 0.5-5 mm. When the closed end is circular, as shown in FIG. 8, the diameter may be 1-10 mm. Experiments show that a 1-2 mm first width and a 1-3 mm second width maintains pnuemoperitoneum.

FIGS. 1A and 1B shows an embodiment of a uterine manipulator wherein the outer tube has a distal ball 88 at outer tube's distal end instead of a disk. Experiments show that a distal ball may be critical to maintaining pnuemoperitoneum as there is less risk of slippage of the ball into the cervical os than a disk when pressure is applies against it. To fulfill this requirement of not slipping into the cervical os, a critical dimension of the ball may have a diameter of ½ inch to 1.5 inches, preferably between 0.65 and 0.85 inches. The distal ball also has the added benefit of covering the hole at the bottom of the stabilizer where the shaft passes through. This prevents loss of pnuemoperitoneum through the cervical os, where the base of the stabilizer with the hole is pressed. The distal ball has the additional benefit of bring atraumatic both upon insertion and retrieval of the device, whereas a disk is atraumatic upon retrieval and may resist withdrawal from the vaginal canal leading the surgeon to use excessive force.

In other embodiments described in this specification, the distal ball may be coupled or combined with an occluder. In other embodiments, the distal ball may be substituted by the occluder.

Additionally, it has been shown that the distal ball has to have a sufficient opening to resist warping from excessive material in tool-making and also to receive a sufficiently strong shaft. Therefore, it has been shown in experiments, that the opening may be between 0.200 inches and 0.300 inches in diameter for receiving a metal shaft that is 0.100 inches to 0.200 inches in diameter.

Figure 9A:
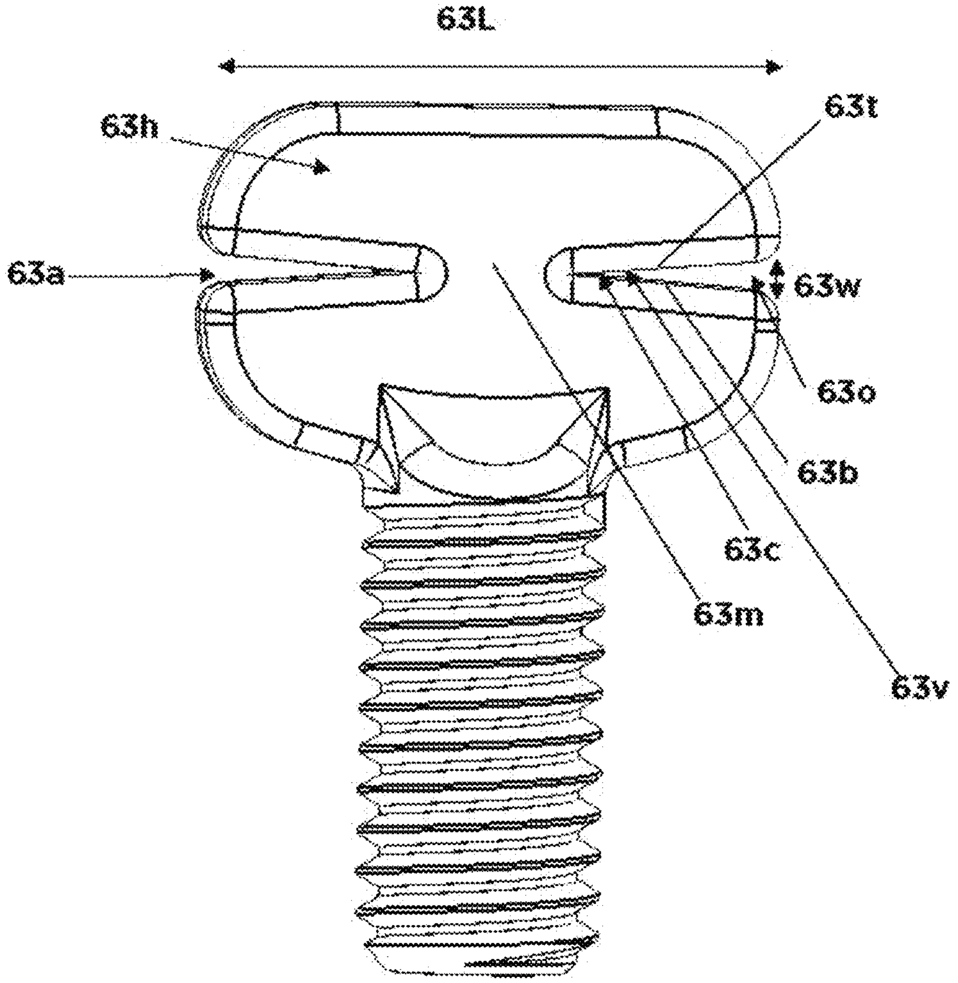
FIGS. 9A-9P show various embodiments of a screw containing crevices.
Figure 9B:
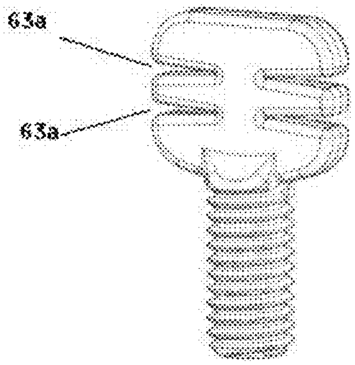
Figure 9C:
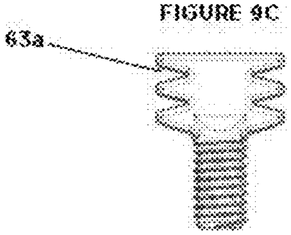
Figure 9D:
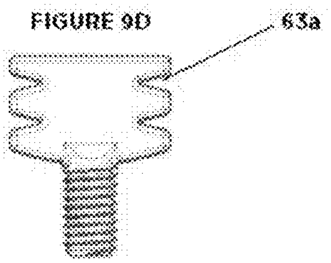
Figure 9E:
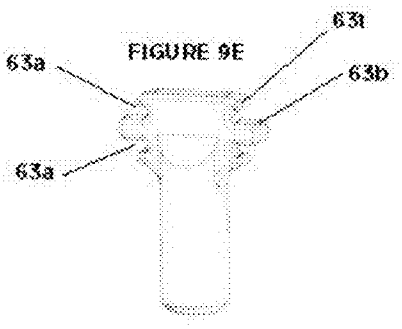
Figure 9F:
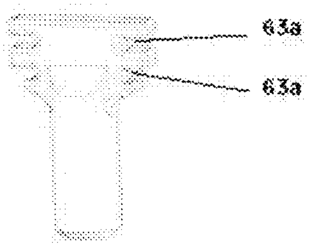
Figure 9G:
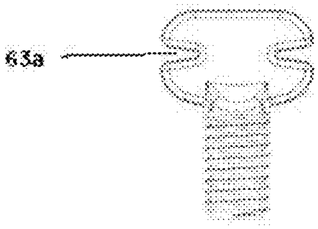
Figure 9H:
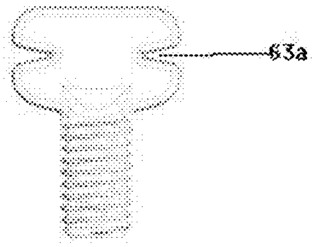
Figure 9I:
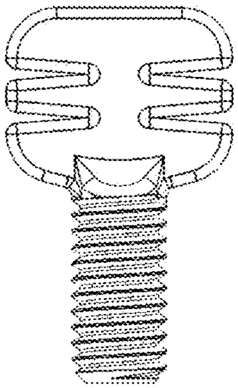
Figure 9J:
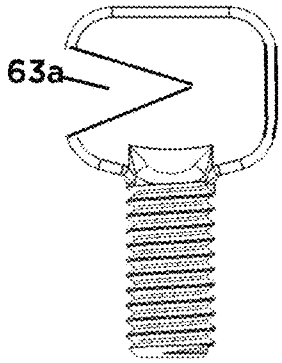
Figure 9K:
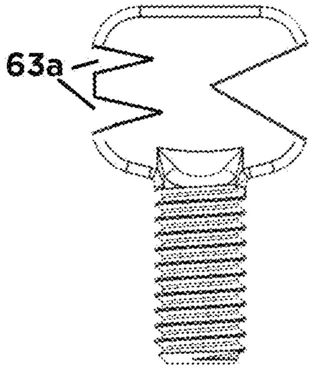
Figure 9L:
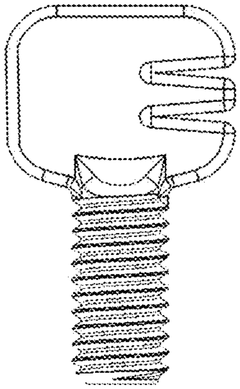
Figure 9M:
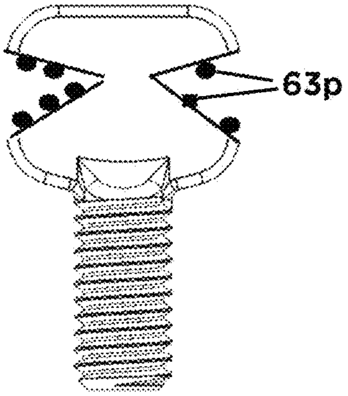
Figure 9N:
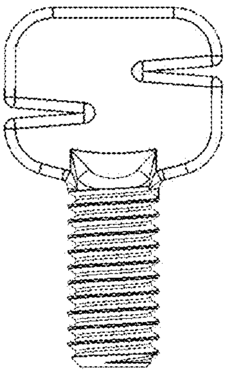
Figure 9O:
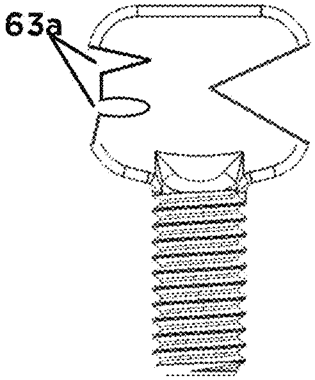
Figure 9P:
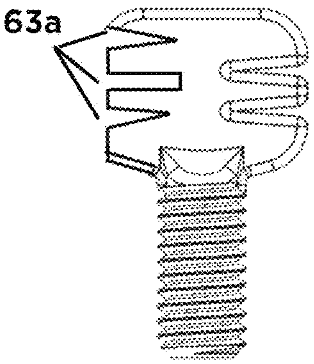

FIGS. 9A-9P show various embodiments of a screw 63 containing indentations, inner wedges, slits, crevices, or cuts (hereinafter "crevices") 63*a* from frontal views and some perspective views (e.g., FIGS. 9B, 9E and 9F). A crevice 63*a* is configured for receiving or tying a cervical stitch or suture to hold the manipulator firmly in place around the cervix and against the vaginal fornices. After applying a stitch to the cervix with a suture's first end and inserting the manipulator, a surgeon may wrap the suture's second free end around screw 63 within crevice 63*a*. Tying the cervical suture around screw 63 pushes the fornix delineator rim closer against the vaginal fornices and cervix for better delineation and definition of the vaginal fornices. Crevice 63*a* is critical to capturing the suture and maintaining the tension of the suture between the fornix delineator and cervix/vaginal fornixes for precise definition of the vaginal fornices and minimum loss of pnuemoperitoneum during colpotomy. Without crevice 63*a*, the suture would risk slipping off the screw 63, and the tension between the fornix delineator and the vaginal fornixes and cervix would be lost. This would lead to imprecise definition of the vaginal fornixes and loss of pnuernoperitoneum, as CO2 would escape through the loose tissue around the fornix delineator rim.

In embodiments, screw 63 may be configured to further secure the manipulator in place by rotating screw 63. Responsive to rotating screw 63, the angular direction of crevices 63A may be changed. Furthermore, by rotating screw 63, stitches positioned within crevices 63A may be tightened or loosened.

A single crevice to receive the stitch or suture may be positioned on the screw (e.g., FIG. 9J), however two or more crevices opposite one another ensure more stable securement of the stick (e.g., FIG. 9A).

FIG. 9A shows an embodiment 63*h* where two crevices are positioned opposite one another in a single row on the screw head. Thus, a stitch may wrap around both crevices for securing the stitch. For example, additional crevices may be added to allow a single stitch to be wrapped around various portions or crevices of the screw.

In other embodiments, multiple rows of crevices may be employed to secure a single stitch or alternatively multiple stitches (e.g., FIG. 9B). For example, if more than one stitch is applied (e.g., one stitch to the posterior cervical lip and another stitch to the anterior cervical lip) then the two stitches may become entangled within the same crevice.

Therefore, an additional row of crevices may be utilized as shown in FIG. 9B to secure the second stitch's free end. Additional rows may be added as required to secure the free ends of additional stiches. Alternatively, the free end of a single stitch may be wrapped around multiple crevices.

In embodiments, one or more crevices 63*a* may be triangular, rectangular (e.g., FIG. 9P) or oval (e.g., FIG. 9O) in shape to receive a suture. In other embodiments, crevice 63*a* may also be any polygonal, square, or mixed shape extending from the side-wall of the screw towards or past the midpoint 63*m* of the screw configured to receive a suture. The crevices may by symmetrical (e.g., FIG. 9B) or asymmetrical (e.g., FIGS. 9K & 9N). The crevices 63A may be V shaped, U shaped, W shaped, or any other curved, polygonal, or mixed shape to allow tying and securing of a suture. Crevice 63*a* may have sharp or curved edges.

In embodiments, crevice 63*a* may be configured to extend into the body of the screw head past a position vertically offset from the circumference of the threaded position of the screw. This may allow the screw to centrally secure the suture within a body of the screw head 63*h*. However, in other embodiments, such as those depicted in FIGS. 9G and 9H, the crevice may not extend into the body of the screw head past a position vertically offset from the circumference of the threaded portion of the screw. In other embodiments, such as FIGS. 9E and 9F, the indentions of different crevices may be different lengths.

As shown in FIG. 9A, crevice 63*a* may extend most or a partial length 63*l* of the screw 63, and may be comprised of an open end 63*o* with a first width 63*w* and a closed end 63*c* with a second width 63*v*, an upper wall 63*t*, and a bottom wall 63*b* between or connecting open end 63*o* and closed end 63*c*.

Upper and bottom walls 63*t* and 63*b* may be parallel (as shown in FIGS. 9E and 9F) or angled (as shown in FIGS. 9A-9D) with respect to one another. Closed end 63*c* may be curved (as shown in FIGS. 9E-9H) or may be comprised of angled walls 63*t* and 63*b* converging to a point (a shown in FIGS. 9A-9D). Alternatively, closed end 63*c* may be rectangular with parallel walls 63*t* and 63*b* (as shown in FIG. 9P). Alternatively, closed end 63*c* may have variable widths that increase and decrease to form a round, closed end.

Upper and bottom walls 63*t* and 63*b* may be equal in length (e.g., FIG. 9F), or unequal (FIG. 9E). Crevices may be mirror images along the y axis, but not along the x axis (as shown in FIG. 9F). Alternatively, crevices may be mirror images along the x axis, but not along the y axis. Crevices 63*a* may be identical in geometry or not identical, as shown in FIGS. 9F, 9K, 9O and 9P)

FIG. 9A shows an embodiment wherein crevice 63*a* extends from the side edge of the screw towards the center of the screw, stopping before the screw's midpoint 63*m*. In other embodiments, crevice 63*a* may extend past the midpoint (e.g., FIG. 9J).

In embodiments, first width 63*w* and second width 63*v* may be identical in width (e.g., rectangular crevice in FIG. 9P). In other embodiments, first width 63*w* and second width 63*v* may not be equal. For example, second width 63*v* may be smaller than the first width 63*w*. This is true, for example, when the crevice is triangular and the top and bottom sidewalk 63*t* and 63*b* narrow to a point (e.g., FIG. 9A).

In some embodiments, first width 63*w* and second width 63*v* are equal or approximately equal, forming a rectangular crevice 63*a* (as shown in FIG. 9P). In other embodiments closed end 63*c* may be curved, so that the second width gradually diminishes (e.g., FIGS. 9E & 9F).

In FIG. 9A, screw 63 has a first crevice on the right half of the screw head and a second crevice on the left half of the screw, opposite one another on the same axis, which are mirror images of one another. However, in other embodiments, the crevices need not be mirror images and need not be on the same axis. A screw may have an odd (e.g., FIG. 9K) or even number of crevices. Alternatively, a first crevice may extend from the screw sidewall horizontally past the midpoint 63*m*, while a second crevice does not extend past the midpoint 63*m* (e.g., FIG. 9O). Any number or shapes of crevices may be on the screw to facilitate capturing a suture. Crevice shapes may be uniform or vary (e.g., FIGS. 9O & 9P)

An embodiment of a screw may have a single crevice 63*a* which may or may not extend past the midpoint 63*m* of the screw. In other embodiments, a column of vertical single crevices may be positioned on the screw without mirror imaged crevices on the other side of the screw (e.g., FIG. 9L). Each crevice in the column may be identical or may vary within shape, size, and may be evenly or unevenly spaced from one another. In embodiments, two columns of crevices may exist opposite one another that are evenly and/or unevenly spaced (e.g., FIG. 9P). Crevices 63*a* may be uniform in shape and size or may be different (e.g., FIG. 9O).

A screw 63 may contain multiple rows of crevices 63*a*. For example, screw 63 may be comprised of a row of two crevices on the same axis (as shown in FIGS. 9A, 9G and 9H) or two rows of two crevices (as shown in the FIGS. 9B-9F). The crevices may be mirror images to one another or may be different shapes and sizes (e.g., FIGS. 9K, 9O, 9P). The crevices may be horizontally or vertically offset from each another, and may be evenly or unevenly spaced.

The crevices may be corrugated or have regular or irregular protrusions 63*p* on the upper sidewall 63*t*, the bottom sidewall 63*b*, and/or the closed end 63*c* to further capture a suture. The protrusions may be angled or rounded edges, and may be spaced evenly or unevenly apart.

Experiments show that for a screw to retain a medical grade suture or stitch, the crevice 63*a* must be sufficiently narrow. As shown in FIG. 9*a*, width 63*w* is between 0.005 and 0.040 inches, preferably 0.020 inches +/−0.005 inches. However, this width may smaller or larger depending on the size of the suture that is employed. In addition a narrowing of the gap to form an angle helps secure the suture; therefore, it is critical that in embodiments containing a triangle or sloping top and bottom sidewalls 63*t* and 63*b*, the angle between the sidewalls be less than 15 degrees to be able to "catch" the suture. In this embodiment, the angle is between 8 and 9 degrees.

In an operation of applying a uterine manipulator, a practitioner would first apply a stitch to the cervix. In a second step, the practitioner may take the free end of the stitch and wrap or tie it around one or more cervices of the screw. Practitioner would repeat the step for any additional stitches.

Figure 10A:
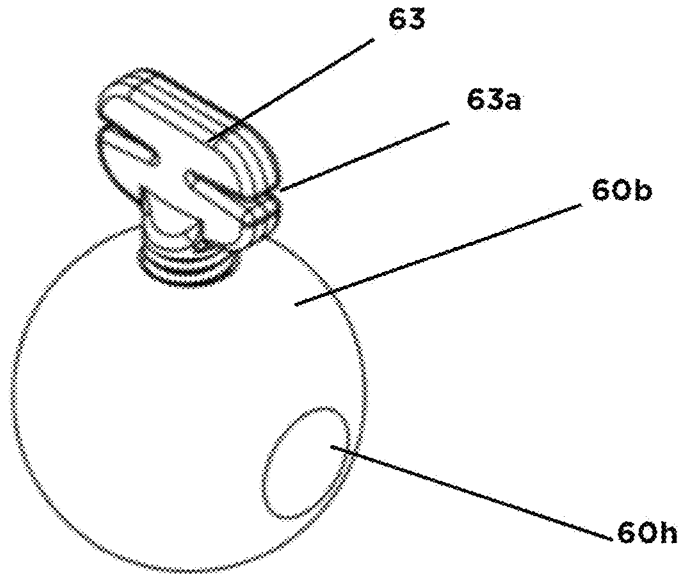
FIGS. 10A-C show a perspective, side and frontal views of an embodiment of a fastener or locking portion that is shaped as a sphere or ball.
Figure 10B:
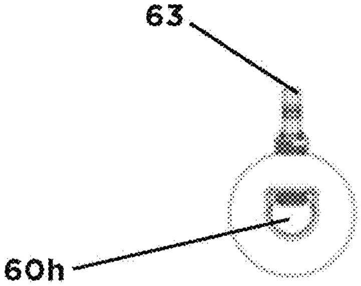
Figure 10C:
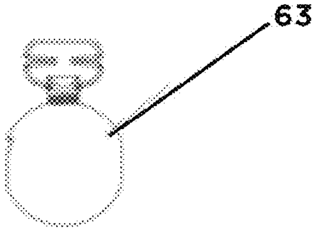

FIGS. 10A-C show a perspective, side and frontal views of an alternative embodiment where the fastener or locking portion 60 is shaped as rounded sphere or ball 60*b*. Ball 60*b* is atraumatic which is critical to minimizing trauma to the vaginal introitus for patients who have extra long vaginal canals and therefore would require the fastener or locking portion 60 to sit within the vaginal canal during use of the uterine manipulator in a procedure. Other embodiments of a fastener or locking portion 60 risk catching vaginal tissue upon insertion and retrieval. The rounded exterior surface of ball 60*b* is configured to prevent tissue catching.

Ball 60*b* may be configured to include a hollow channel 60*h* extending through a body of the ball and designed receive the shaft 31 of the manipulator. Ball 60*b* may be integrated as one piece with the outer tube 61 and/or distal ball 88, or be separate pieces, as shown in FIG. 1. In addition, ball 60*b* may be integrated with an occluder, such as those described, referenced, or incorporated in this specification. Integration has the added benefit of ease of use for the clinician who does not have move multiple parts.

Figure 10D:
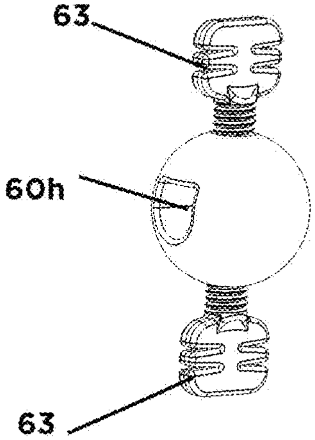
FIGS. 10D-F shows perspective, side and frontal views respectively of an embodiment of a ball configured to hold multiple screws.
Figure 10E:
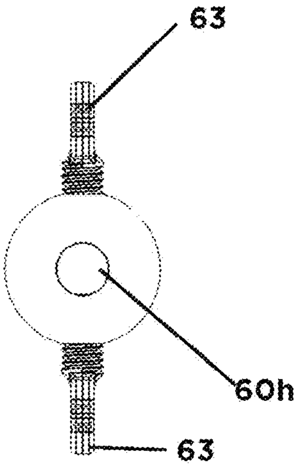
Figure 10F:
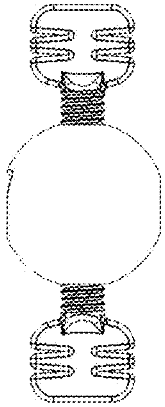

FIGS. 10D-F shows perspective, side and frontal views respectively of an embodiment of ball 60*b* configured to hold multiple screws 63. Ball 60*b* may include one or more threaded passageways configured to receive one of more screws 63, as shown in FIG. 10A, or may receive multiples screws as shown in FIG. 10D. For example, a screw may be positioned on the bottom portion of the ball, and another second may be on the top portion of the ball as shown in FIGS. 10D-F.

In an operation of a uterine manipulator, the double screws allows a surgeon to wrap a stitch attached to the posterior cervical lip to the bottom screw, and then attach a stich attached to the anterior cervical lip to the top screw, or vice-versa. In other words, two sutures may be placed on the cervix and pass through separate stabilizer windows or slits and may be affixed, wrapped or tied around separate screws to avoid entanglement. Two screws enable a surgeon to tie each string/suture to a separate screw and avoid entanglement.

The two screws may be symmetrically or asymmetrically placed. The two screws may be positioned one hundred eighty degrees apart along the circumference of fastener or locking portion 60. Each of the two screws may be independently rotated such that the angular offset of crevices 63*a* between each screw 63 may be changed. The fastener or locking portion 60 may be configured to receive even two or more screws (3, 4, 5), etc., as may be needed.

FIGS. 11A-C show a perspective, side and frontal different views of another embodiment of a fastener or locking portion 60 configured for receiving two screws 63 with crevices 63*a*. FIGS. 12A-C show an embodiment configured for one screw 63 with crevices 63*a*.

Figure 13C:
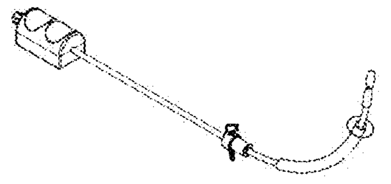
FIGS. 13A-13C show side, frontal, and perspective views respectively of an embodiment of a manipulator with a curved L or J shaped shaft.
Figure 13A:
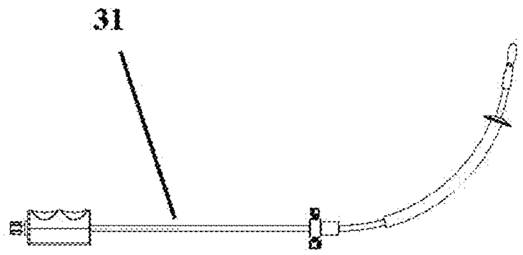
Figure 13B:
Figure 13F:
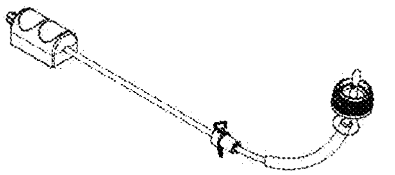
FIGS. 13D-13F show side, frontal, and perspective views respectively of an embodiment of a manipulator with a fornix delineator with a curved L or J shaped shaft.
Figure 13D:
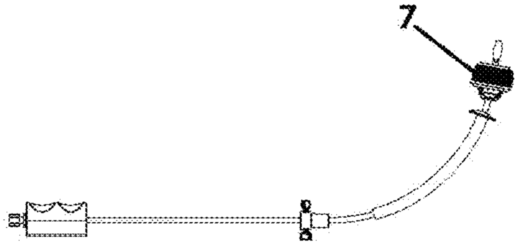
Figure 13E:
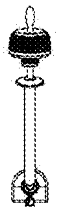

FIGS. 13A-13F show another embodiment of a manipulator with a curved L or J shaped shaft. FIGS. 13A-C show a simple manipulator intended for general manipulation without colptomy, and therefore without fornix delineator in a side, frontal and perspective view respectively. FIGS. 13D-13F show an embodiment including a fornix delineator, which in this embodiment is a collar 10 coupled to stabilizer 20. However, in embodiments, collar 10 may be substituted by alternative fornix delineators, such as cups 8, pronged cups 6, alternative collars 10, stabilizers 20, and other market and readily available fornix delineators. Embodiments may have substituted part, features, variations or embodiments described, referred or incorporated herein. For example, embodiments may include a distal ball 88 in lieu of a disk; a ball fastener or locking portion 60*b* instead of a cylindrical fastener or locking portion; and/or a string 64 and ring 65 (as shown in FIG. 1). Embodiments may also include an occluder described herein. In embodiments, a handle 32 of the uterine manipulator device may be substantially planar with shaft 31.

Figure 14C:
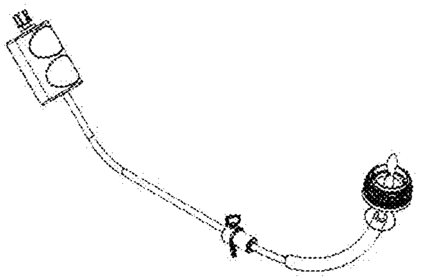
FIGS. 14A-14C show side, frontal, and perspective views respectively of an embodiment of a uterine manipulator device with a curved L shaped shaft with a proximal angled handle portion and a fornix delineator.
Figure 14A:
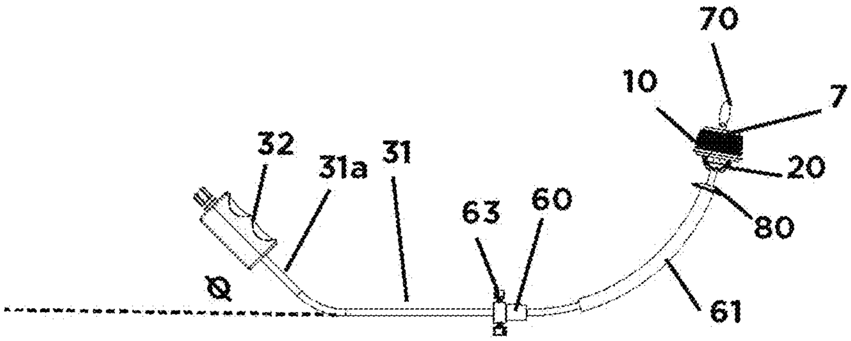
Figure 14B:
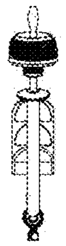
Figure 14F:
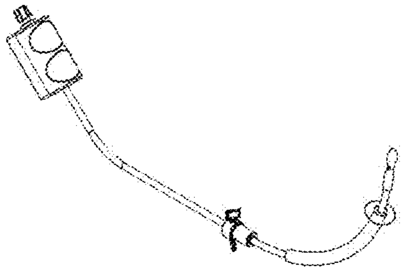
FIGS. 14D-14F show side, frontal, and perspective views respectively of an embodiment of a uterine manipulator device with a curved L shaped shaft with a proximal angled handle portion without a fornix delineator.
Figure 14D:
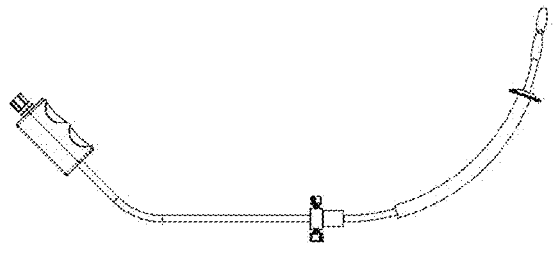
Figure 14E:
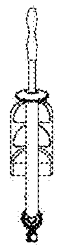

FIGS. 14A-14C show different perspective views of an embodiment of a uterine manipulator device with a curved L shaped shaft 31 with a proximal angled handle portion 31*a*. FIGS. 14A-14C show an embodiment including a stabilizer and collar, while FIGS. 14D-14F show an embodiment of simple manipulator without a collar or stabilizer. However, in embodiments, collar 10 may be substituted by alternative fornix delineators, such as cups 8, pronged cups 6, alternative collars 10, stabilizers 20, and other market and readily available fornix delineators. Embodiments may have substituted part, features, variations or embodiments described, referred or incorporated herein. For example, embodiments may include a distal ball 88 in lieu of a disk; a ball fastener or locking portion 60*b* instead of a cylindrical fastener or locking portion; and/or a string 64 and ring 65 (as shown in FIG. 1). Embodiments may also include an occluder described herein.

The angled portion 31*a* forms an angle ⦰ of less than 90 degrees with the longitudinal portion of the shaft. The angled handled portion 31*a* enables superior leverage and manipulation of the cervix. It also reduces the fatigue of a nurse or practitioner who may be required to hold the manipulator for extended hours. The angled portion enables the nurse to more easily pivot the device upward and downward, in addition to moving it 360 degrees and to the left and right. The angled portion obviates the need for a nurse to bend forward to bend, lean or reach down, which may be true in the L shaped configurations where the vaginal introitus and handle 32 are positioned below the resting position of the hand when the nurse or practitioner is standing or sitting at the operating table.

Figure 15A:
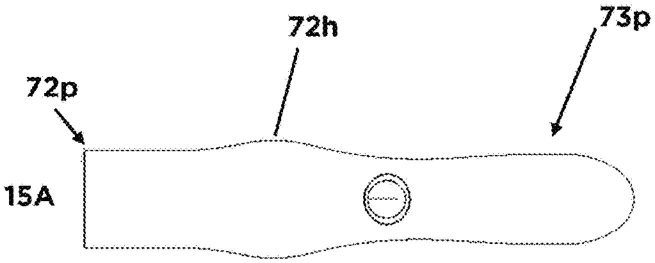
FIG. 15A shows an embodiment of a tip with a proximal hump but without a distal hump.

FIG. 15A shows an embodiment of tip 70 containing a single proximal bump, distension, or hump 72*h* (hereinafter "hump 72*h*") with a diameter larger than the distal tip portion 73*p* diameter, which does not have a pronounced hump, though the sidewalls gradually slope out before sloping inward to form a rounded, distal tip. Other embodiments may have a single distal hump 73*h* and no proximal hump 72*h*.

Figure 15B:
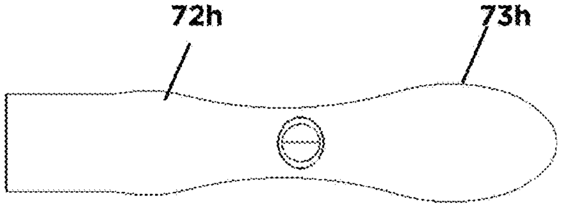
FIG. 15B shows an embodiment of a tip with a distal hump greater in diameter than a proximal hump.
Figure 15C:
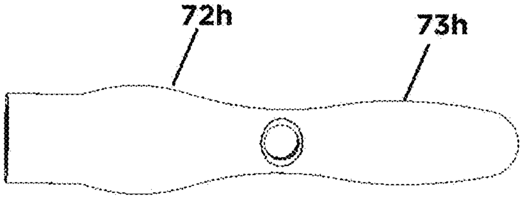
FIG. 15C shows an embodiment of a tip with a proximal hump greater in diameter than a distal hump.

FIG. 15B shows an embodiment of tip 70 having distal hump 73 that is greater in diameter than proximal hump 72. Whereas, FIG. 15C shows an embodiment of tip 70 having a first proximal hump 72*h* that is greater than the diameter of the distal hump 73*h*. In embodiments, both the proximal hump 72*h* and distal hump 73*h* may have diameters that are greater than the smallest diameter of the tip.

Figure 15D:
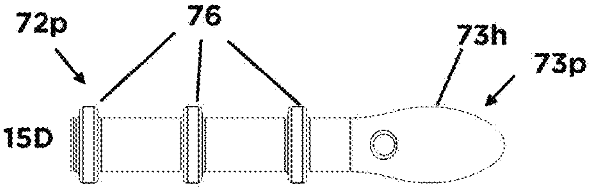
FIGS. 15D and 15E show a side and perspective view of an embodiment of a tip with a distal hump and rings proximal to the distal hump.
Figure 15E:
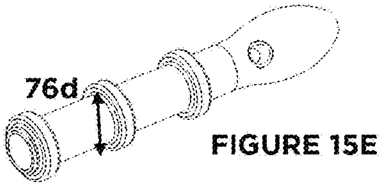
Figure 15F:
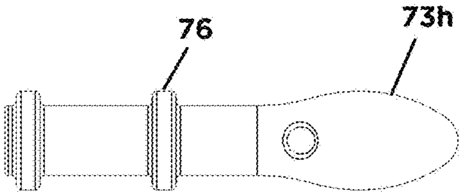
FIGS. 15F and 15G show a side and perspective view of an embodiment a tip wherein the tip includes only two rings.
Figure 15G:
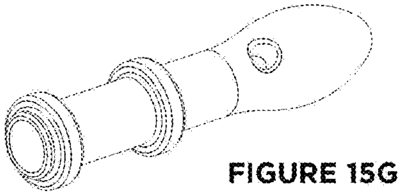

FIGS. 15D and 15E show a side and perspective view a tip 70 wherein the tip only has a single distal hump 73*h*, and no proximal hump 72*h*. In addition, tip 70 includes rings 76 encircling the body of the tip proximal to the distal hump 73*h*. Rings 76 have a diameter 76*d* greater than the diameter of the narrowest portion of the tip 70. Diameter 76*d* also exceeds the diameter of the tip's proximal portion 72*p*. The rings 76 serve as a means for a physician to feel the depth of insertion into the cervical os and resist slippage of the tip from the cervical os. FIGS. 15F and 15G show a side and perspective view a tip 70 wherein the tip includes only two rings.

Any number of rings (1, 2, 3, or more) may be positioned on any portion of any tip embodiment described, referred or incorporated herein. Rings 76 may be evenly or unevenly spaced and may vary in size. Rings 76 may be positioned on tips with a proximal hum 72*h* and distal hump 73*h*, or on embodiments having only a proximal hump. Rings may 76 be positioned on the proximal portion 72*p* or distal portion 73*p*, or both.

Ring diameter 76*d* may be equal or exceed the diameter of distal hump 73*h*. For embodiments with a proximal hump 72*h*, ring diameter 76*d* may exceed the proximal hump diameter. Ring diameter and thickness 76*d* may vary across rings on the same embodiment, or may be uniform. Rings 76 may have smooth or irregular surfaces. The surfaces may be patterned with protrusions which are evenly or unevenly spaced.

Figure 15H:
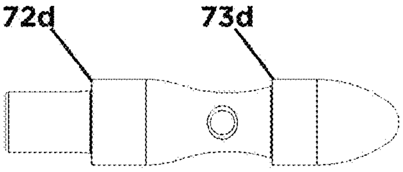
FIG. 15H and FIG. 15I show a side and perspective view of an embodiment a tip.
Figure 15I:
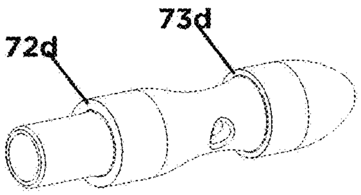

FIG. 15H and FIG. 15I show a side and perspective view a tip 70 where the proximal hump 72*h* and distal hump 73*h* do not gradually slope at their proximal portions, bur rather have a ledge, ridge, or discontinuous drop (hereinafter "drop") 72*d* and 73*d* comprised of a surface perpendicular to the surface of the tip's sidewalls. Any number of drops may be positioned on the tip, at the proximal, middle or distal portions. The advantages of such drops is that prevent the tip from sliding out of the cervical os of the patient but providing an additional surface of resistance.

FIGS. 16A-16F illustrate various positions and configurations of holes 71 on a tip 70. These configurations are illustrative, and any configuration of holes on one embodiment of tip may be positioned on another embodiment tip. Furthermore, holes may be added or removed from a configuration. Holes may be positioned along any portion of the tip, though placing the holes on the sidewall rather than at the distal tip maximizes the chance of dye delivery and minimizes the risk of occlusion via the uterine wall.

Figure 16A:
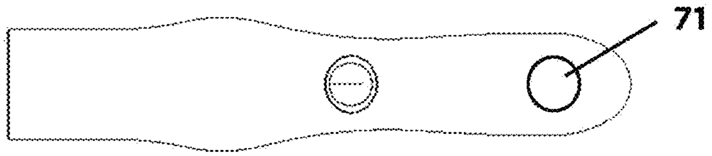
FIGS. 16A-16F illustrate various positions and configurations of embodiments of holes on a tip.
Figure 16B:
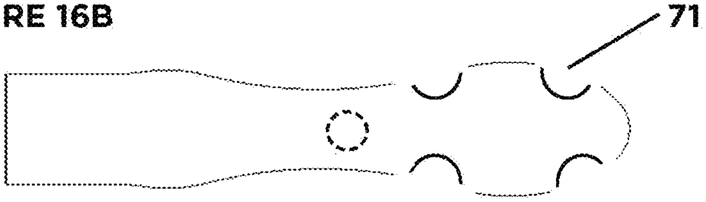
Figure 16C:
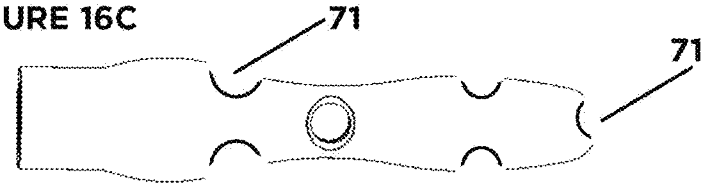
Figure 16D:
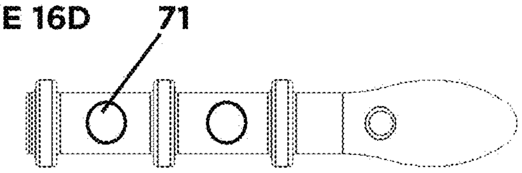
Figure 16E:
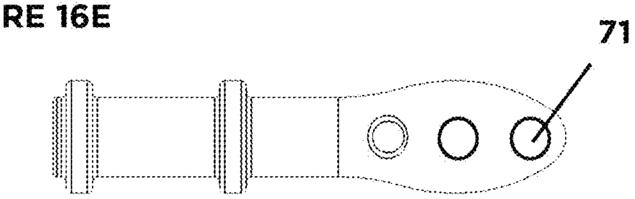
Figure 16F:
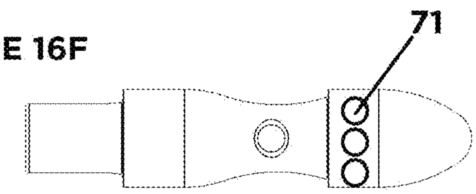

FIG. 16B shows an embodiment wherein the holes are positioned radially around the tip circumference before and after distal hump 73*h*, along the sloping walls. FIG. 16B shows an embodiment wherein the holes are positioned also distal to the proximal hump 72*h*. FIG. 16D shows an embodiment wherein the holes are positioned along the sidewalk between rings 76. FIG. 16E shows an embodiment wherein the holes are positioned along the walls at the distal portion 73*p* on a longitudinal axis. FIG. 16F shows an embodiment wherein the holes are positioned radially around the tip circumference on hump 73*h*. Holes may also be positioned on proximal hump 72*h*.

In other embodiments of a uterine manipulator, a simple balloon tip may be utilized which may inflate to a spherical or oval shape, or any of the shapes described herein.

Figure 17A:
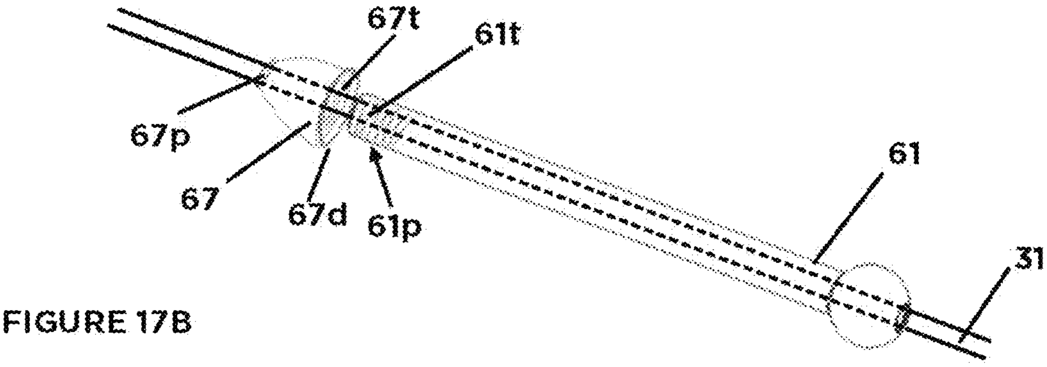
FIGS. 17A-B show an embodiment of a cap configured to couple to the distal end of an outer tube.
Figure 17B:
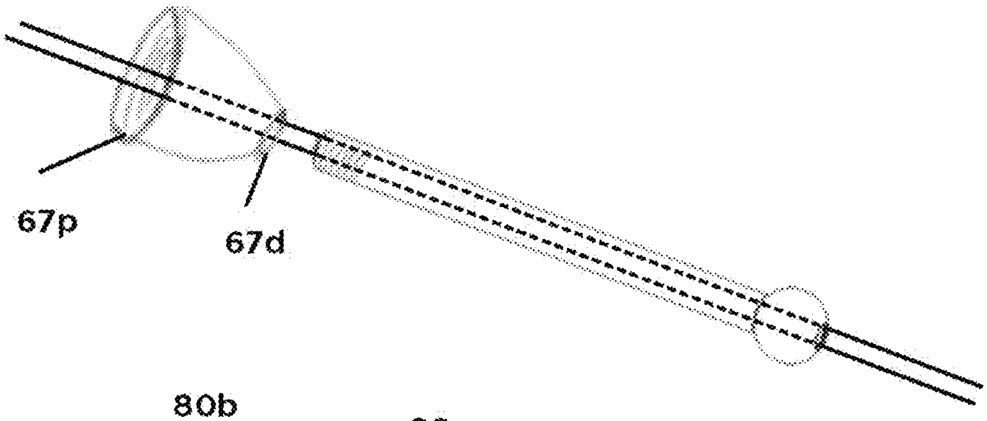

FIGS. 17A-B show another embodiment of an outer tube 61 wherein the outer tube's proximal end 61*p* is configured to receive a cap 67, comprised of a proximal end with a first proximal opening 67*d* and a distal end with a first distal opening 67*d*, and a hollow inner cavity 67*c* on the inner surface between the proximal and distal openings. As shown, proximal opening 67*d* is configured to be larger than the diameter of shaft 31, to enable sliding of the cap along the shaft 31. Distal opening 67*d* may be configured to be larger than the diameter of the outer tube (and be extension shaft 31) to facilitate coupling of cap 67 to outer tube 61.

Both the cap 67 and outer tube 61 are positioned on a shaft 31 of a medical device or manipulator. Responsive to a practitioner positioning or coupling a cap 67 to the outer tube 61, the outer tube's diameter constricts or lessens so that the outer tube is pressed against the shaft, fixed in position, and not movable along the shaft 31. Moving the outer tube requires a force exceeding the friction force of the outer tube 61 in contact with the shaft 31. The advantage of the cap 67 is that it may slide inside the vaginal canal atraumatically and obviates the need for tightening screws 63, which may be traumatic to tissue when inserted into a patient's introitus or vaginal canal. Thus, the fastener or locking portion 60, comprised of a ball 60*b* and screw 63, may be substitute by cap 67.

In the embodiment shown in FIG. 17*a*, the diameter of the cap's 67 distal opening 67*d* is larger than the proximal opening 67*p*. In the embodiment of FIG. 17B, however, the diameter of the cap's 67 distal opening 67*d* is smaller than the diameter of the proximal opening 67*p*. In this embodiment of FIG. 17B, the larger diameter of the proximal opening 67*p* serves an occluding function, preventing the loss of pnuemoperitoneum from the vaginal canal during colpotomy. Thus, the cap 67 serves both a fixing function (securing the outer tube in position), in addition to an occluding function.

To facilitate securing cap 67 onto the outer tube 61, the inner surface of the cap may include threads 67*t* and the outer surface of tube 61 may include corresponding threads 61*t* at the coupling end, which enable the cap 67 to screw onto the outer tube. Thus, when the cap 67 is screwed onto the outer tube, the outer tube compresses or restricts in diameter, the outer tube is prevented from sliding forward or back via friction against the shaft 31. However, in other embodiments, cap 67 an outer tube need not include threads to achieve the tightening or screwing functions. Cap 67 and outer tube may have alternative mating systems.

In embodiments, distal opening 67*d* may be configured to be smaller in diameter than the outer tube so it is configured to screw into and couple into the space between the outer tube's inner wall and shaft 31. In embodiments, threads may be positioned on the inner wall of the outer tube, and corresponding threads may be positioned on the outer surface of the cap at the distal opening 67*d* to facilitate coupling.

Figure 17C:
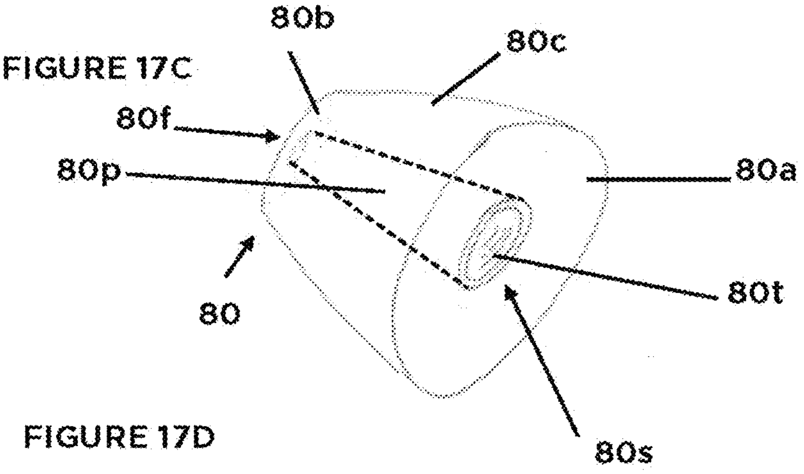
FIG. 17C illustrates an embodiment of occluder which functions as a cap.

FIG. 17C illustrates an embodiment of cap 67 which may also serve as an occluder 80, and thus may be convexly shaped with a curved outer surface. This embodiment is comprised of a proximal end with a first opening 80*f* and a second opening 80*s*, and an inner conduit or passage 80*p* coupling the first and second openings, an outer surface or circumference 80*c*. Both openings may be configured to be larger than the diameter of shaft 31, to enable sliding of the occluder along the shaft 31. The diameter of the second opening 80*s* is greater than the diameter of the first opening 80*f*. Either the first opening 80*f* or second opening 80*s* may be configured to couple to the outer tube's proximal end 61*p*, such that when the outer tube is coupled to the occluder 80, it is no longer slideable or movable along shaft 31.

Occluder 80 may fix the position of the outer tube in place be reducing or tightening the diameter of the outer tube 61 around the shaft 31 when the first or second opening is coupled to the outer tube. In this embodiment, the compression of the outer tube against the shaft and resulting friction between the outer tube and shaft prevents movement. To facilitate coupling and reduction of the outer tube diameter, inner conduit 80*p* may include threads or a threaded portion 80*t* and outer tube's proximal end 61*p* may include corresponding threads 61*t*, so that the occluder 80 may screw onto outer tube 61 and reduce the diameter of the outer tube.

In the embodiment of FIG. 17C, occluder may be comprised of foam or sponge. Alternatively, it may be a balloon with a lumen and leer lock to inflate air after or before coupling to the outer tube 61. Alternatively it may be plastic or some other flexible, biocompatible material. Inner conduit 80*p* may be comprised of a plastic, metal, ABS, PC, or other hard material to enable threads. Similarly, the outer tube may include a plastic, metal, ABS or PC material to enable threads. A foam or sponge may be over or insert molded inner conduit 80*p*.

In an embodiments, inner conduit 80*p* may be one material, such as a plastic, while the remaining occluder 80 is sponge or foam. In addition, some or all of the surface of the occluder may also be covered in a non-porous coating or material to prevent CO2 leak or loss of pnuemoperitoneum through, for example, sponge or foam. For example, first opening 80*f*, second opening 80*s*, and/or the outer circumference 80*c* may have a non-porous coating. However, the material between outer circumference 80*c* and inner passage 80*p* may be a foam, sponge, or other material referenced in this specification.

In embodiments, occluder 80 may be permanently fixed or coupled to the outer tube via over-molding or some other method. When permanently fixed, occluder and outer tube may be fixed into position be a secondary cap, or ball and screw, pin, or other locking mechanism described, referenced or incorporated herein or other general locking mechanism.

Figure 17D:
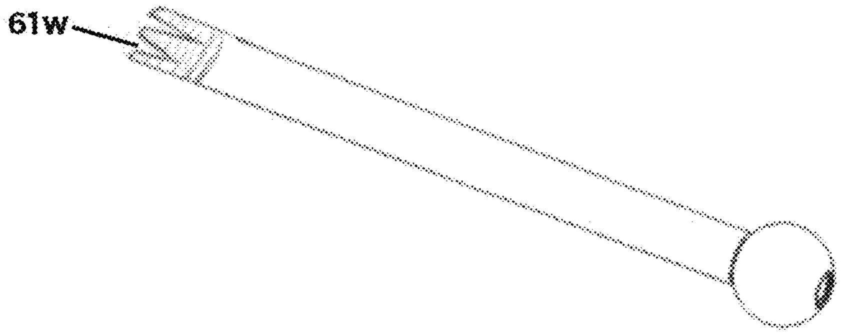
FIG. 17D shown an embodiment of an outer tube with slits, crevices or wedges.

As shown in FIG. 17D, to facilitate tightening, the outer tube may have slits, crevices or wedges (hereinafter "wedges 61*w*"). Wedges 61 enable the outer tube to flexibly restrict the diameter of the outer tube, particularly when the outer tube is made of a harder material. Responsive to a cap 67 or occluder 80 being tightened around the wedges, the wedges restrict in diameter and tube tightens and the outer tube is fixed into position.

In embodiments, wedges 61*w* may triangular, rectangular or oval in shape. In other embodiments, wedges 61*w* may also be any polygonal, square, or mixed shape extending from the proximal end of the outer tube 61 towards the distal end. The wedges may by symmetrical or asymmetrical. The wedges may be V shaped, U shaped, W shaped, or any other curved, polygonal, or mixed shape to allow tying and securing of a suture. The wedges may have sharp or curved edges. Wedges may by symmetrical or asymmetrical. The variations and embodiments of previously described crevices 63*a* also apply to wedges 61*w*.

Figure 17E:
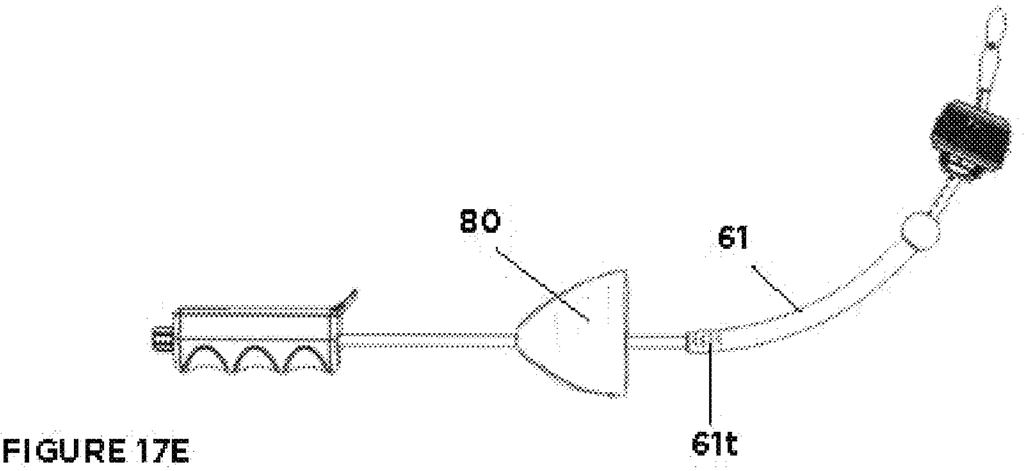
FIGS. 17E and 17F illustrate an embodiment of a uterine manipulator including a cap or occluder in a first position and in a second position, respectively.
Figure 17F:
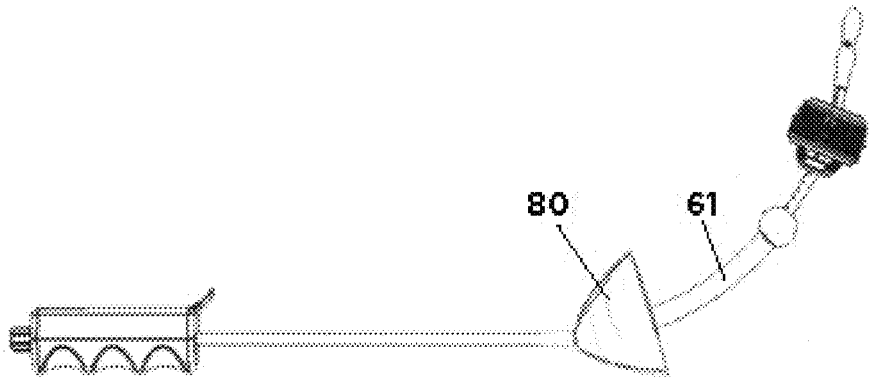

FIGS. 17E and 17F illustrate an operation of an embodiment of a uterine manipulator including a slidable occluder 80 in a first position (FIG. 17E), and then coupled to outer tube 61 in a second position (FIG. 17F). In this embodiment, second opening 80*s* is configured for coupling to the outer tube. An alternative variation of this embodiment is where cap 67 is substituted for occluder 80, the difference being the cap has a hollow inner cavity 67*c*, whereas the occluder may be comprised of material (e.g., foam or sponge, etc.) except for inner passage 80*p*. In yet another embodiment, occluder 80 or cap 67 is permanently coupled to outer tube and not slideable, appearing as FIG. 17F.

Figure 17G:
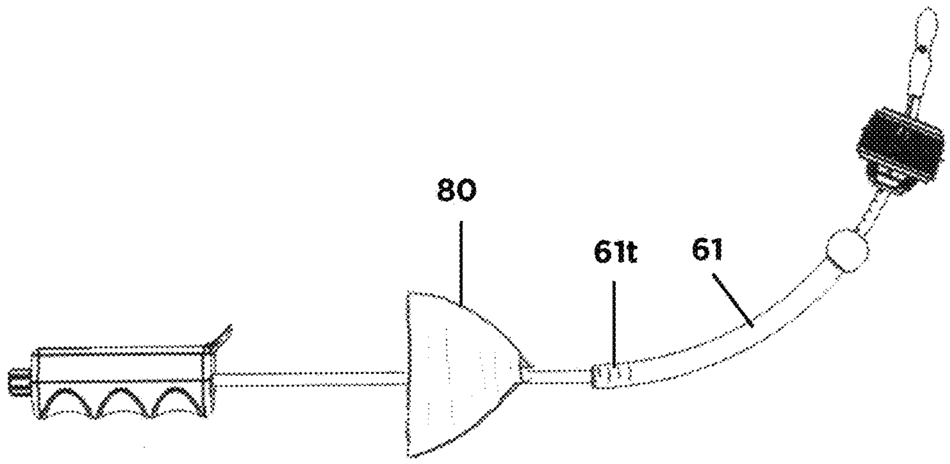
FIGS. 17G and 17H illustrate an embodiment of a uterine manipulator including a cap or occluder in a first position and in a second position, respectively.
Figure 17H:
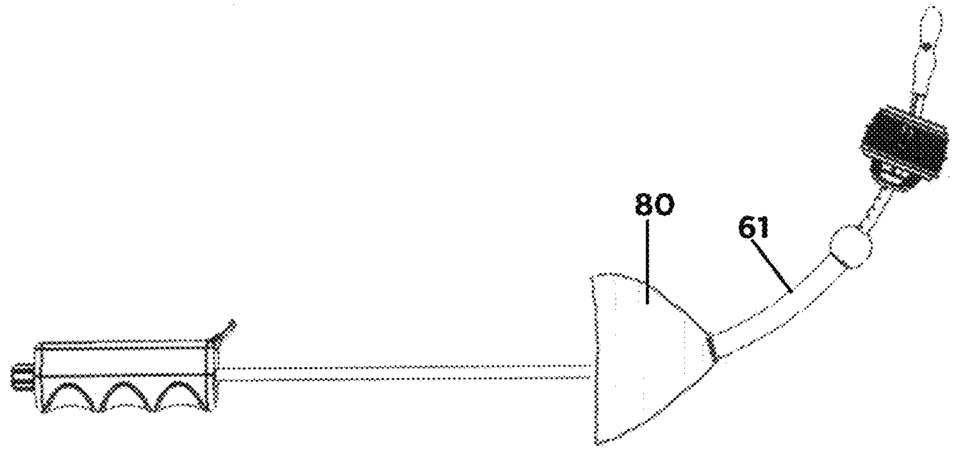

FIGS. 17G and 17H illustrate an embodiment of a uterine manipulator including a slideable occluder 80 in a first position (FIG. 17G), and then coupled to outer tube 61 in a second position (FIG. 17H). In this embodiment, first opening 80*f* is configured for coupling to the outer tube. An alternative variation of this embodiment is where cap 67 is substituted for occluder 80, the difference being the cap has a hollow inner cavity 67*c*, whereas the occluder may be comprised of material (e.g., foam or sponge, etc.) except for inner passage 80*p*. In yet another embodiment, occluder 80 or cap 67 is permanently coupled to outer tube and not slideable, appearing as FIG. 17H.

Figure 18A:
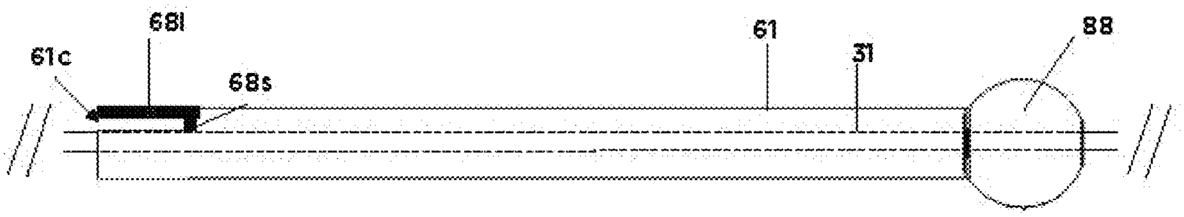
FIGS. 18A-B depict side views of an embodiment of an outer tube with a stop.
Figure 18B:
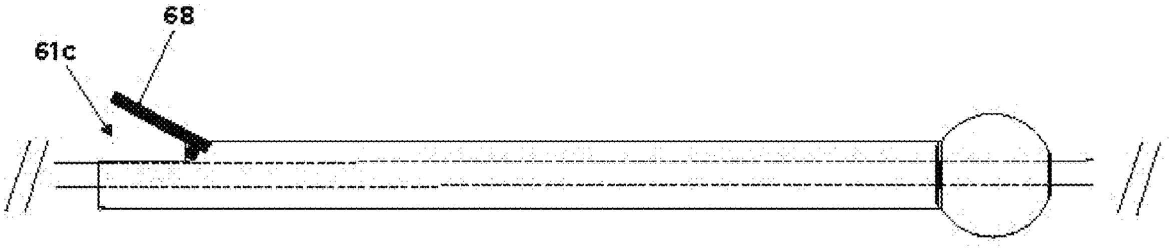

As illustrated in FIGS. 18A-G, outer tube 61 may also be integrated with fastener or locking portion 60 that secures the outer tube 61 onto a desired portion of the uterine shaft 31. In embodiments, outer tube 61 may have a cutout 61*c* to receive a stop 68 with a long portion 68*l* and short portion 68*s*, wherein the long portion 68*l* is flush or parallel to the outer tube, and the short portion 68*s* is angled or perpendicular with respect to the outer tube. A pin 68*p* may traverse through stop 68 to couple to outer tube 61, and also allowing rotational movement of the stop around the pin. As shown in FIG. 18A, when the long portion 68*l* is flush with the outer tube, the short portion 68*s* is in contact with shaft 31 and prevents the outer tube from sliding forward or back. As shown in FIG. 18B, responsive to lifting the long portion 68*l*, short portion 68*s* is released from contact with shaft 31 and allows movement of the outer sliding tube.

Figure 18C:
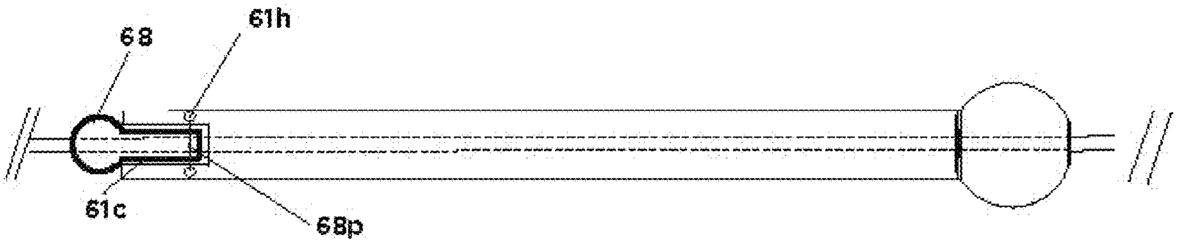
FIG. 18C shows a top view of an embodiment of an outer tube with a stop.
Figure 18D:
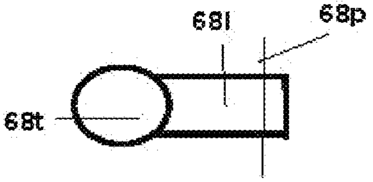
FIG. 18D-18E show a top and perspective view respectively of an embodiment of a stop.
Figure 18E:
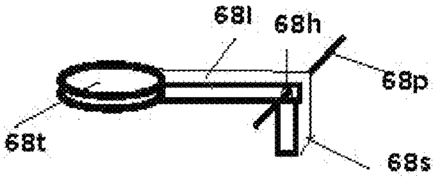

FIG. 18C shows a top view of stop 68 with respect to outer tube 61, and in particular rectangular cutout 61*c*. Outer tube may include one or more holes 61*h* to receive the stop's pin 68*p*. FIGS. 18D & 18E shows a top view and perspective view of stop 68 respectively and illustrate how stop 68 may also include an ergonomic thumb portion 68*t* with a larger width or diameter than the stop's inner portion 68*i* positioned within cutout 61*c*. Stop 68 may also include a hole 68*h* to receive pin 68*p* at the juncture between the long portion 68*l* and short portion 68*s*.

Figure 18F:
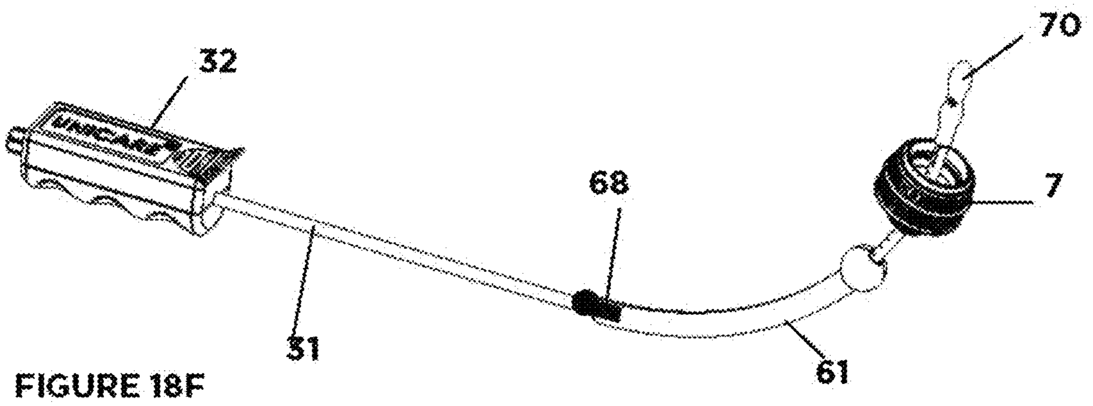
FIG. 18F-18G show a perspective and side view respectively of an embodiment of a uterine manipulator with a stop.
Figure 18G:
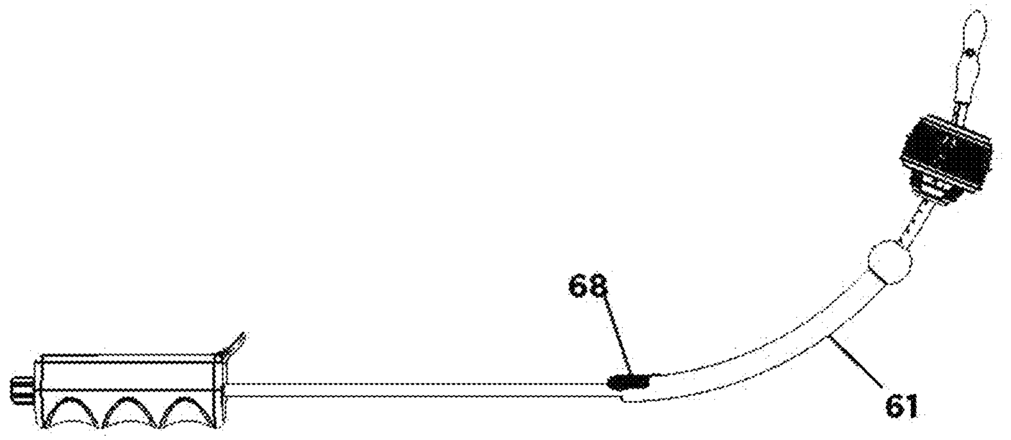

FIGS. 18F and 18G show stop 68 in an embodiment of a uterine manipulator in an unlocked position. Any embodiments of constituent parts shown, described, or referenced may be substituted. For example, a stop 68 may be part of a uterine manipulator with fornix delineator that is a cup 8 or pronged cup 6, rather than a collar 10. In addition, a ring 65 and string 64 may be added to the embodiment and coupled to the fornix delineator 7.

Stop 68 may substitute a ball 63*b* and screw 63. The advantage of the stop 68 is that is atraumatic to the vaginal introitus is positioned within the vaginal canal and is faster to deploy than a screw mechanism. Stop 68 may also include crevices 68*c* (similarly described to crevices 63*a*) configured to receive stitches or sutures along the stop's sidewalls or thumb portion 68*t*. For example, a crevices 68*c* may be triangular, rectangular, or oval in shape to receive a suture. In other embodiments, crevice 68*c* may also be any polygonal, square, or mixed shape. The crevices may by symmetrical or asymmetrical. Crevices 68C may be V shaped, U shaped, W shaped, or any other curved, polygonal, or mixed shape to allow tying and securing of a suture. Crevice 68*c* may have sharp or curved edges.

The stop mechanism for fixing the outer tube in position described includes a pin. However any stop mechanism may be substituted, for example, a spring loaded mechanism, or non-pin-based system.

FIG. 19A shows an embodiment of a uterine manipulator with an occluder 80. Various occluders 80 may be employed with manipulator to prevent the lost of CO2 or pnuemoperitoneum during a colpotomy. As shown in FIG. 19A, an occluder 80 may be positioned at various portions along a manipulator; in position "A" between the handle and fastener or locking portion 60; position "B" on or adjacent fastener or locking portion 60; position "C" on outer tube 61; position "D" on or adjacent to the distal portion of the outer tube 61 or distal ball 88; or position "E" between distal portion of the outer tube 61 or distal ball 88 and fornix delineator. During colpotomy, however; it is critical is that the occluder positioned at the vaginal introitus or within the vaginal canal to prevent loss of CO2. An occluder may be fixed in one position or may slide between positions.

In embodiments, an occluder may be comprised of a sponge, foam or other similarly malleable or flexible material. However sponge or foam material may allow air leak through the porous matter. Therefore, in embodiments, the sponge or foam may be coated in part or whole by a non-porous flexible biocompatible material (e.g., polyurethane, polyolefin, plastics, latex, rubber, synthetic fibers, nylon, rubber, Silicone (Polydimethylsiloxane), Polyurethane (e.g., Aliphatic Aromatic), Polycarbonate Urethane, Polyvinyl Chloride (PVC), Polyethylene Mesh or Film LLDPE, LDPE, HDPE, Polypropylene Mesh or Film, Nylon, Pebax, Polycarbonate, or other materials or other resins that allow the foam or sponge to retain flexibility). In embodiments, the non-porous material may cover the sponge or foam in totality. However, this may lead to rigidity and difficulty when inserting into the vaginal canal. Therefore, a preferred embodiments are where the non-porous material 81 covers only a portion of the sponge or foam.

FIG. 19B shows an embodiment of an occluder shaped as a disk wherein the sponge has a first surface 80*a*, a second surface 80*b*, a circumference 80*c*, and hole 80*h* in the middle portion to permit passage of shaft 31 or outer tube 61. In embodiments, sponge or foam may coated with non-porous material 81 on the first surface 80*a*, a second surface 80*b*, and/or the circumference 80*c*. FIG. 19B shows an embodiment where circumference 80*c* is coated in non-porous material 81. In other embodiments, the non-porous material may be coated on the surfaces of both sides, or simply a single surface. However, a single side or surface coating allows the foam or sponge material to retain it's flexible character for insertion and retrieval. Embodiments with non-porous coating 81 on a single surface may have the coated surface on the proximal side of the occluder, closer to the vaginal introitus. This helps prevent air leak or loss of CO2 during colpotomy. Other embodiments may have the porous coating on the distal side of the occluder, closer to the uterus. In other embodiments, the coating may be positioned also on the circumference of the disk. In a disk embodiment, the disk may be at least 2 inches wide, and at least a ½ inch thick, depending on the vaginal anatomy.

FIG. 19E shows an embodiment of a sponge or foam occluder with crevices 80*w* configured for allowing passage of stitches or sutures from the cervix to a portion of the manipulator, such as the screw. In embodiments, sponge or foam occluders may include crevices 80*w* that may be the same shape or substantially the same shape as screw crevices 63*a*. These crevices permit the suture to pass through the occluder without compressing the occluder leading to a CO2 leak.

A preferred embodiment is where crevices 80*w* are narrow slits to limit the loss of pnuemoperitoneum or CO2. However, in other embodiments, crevices 80*w* may triangular, rectangular or oval in shape. In other embodiments, crevices 80*w* may also be any polygonal, square, or mixed shape. Crevices 80*w* may by symmetrical or asymmetrical. Crevices 80*w* may be V shaped, U shaped, W shaped, or any other curved, polygonal, or mixed shape to allow tying and securing of a suture. Crevices 80*w* may have sharp or curved edges. Crevices 80*w* may by symmetrical or asymmetrical.

In other embodiments an inflatable balloon may be utilized as an occluder. As shown in FIG. 19D, a balloon occluder 80 may include an inlet port 86 or luer lock and lumen 87, and may be inflated into any shape such as a disk or donut shape with a hole 80*h* positioned in relatively the middle to allow passage of shaft 31.

FIGS. 19C, 19F, and 19G show alternative embodiments of an occluder with differing shapes. As shown, an occluder may be a cylindrical, conical, circular, oval, polygonal, mixed, regular, irregular, symmetrical or asymmetrical shape. Occluder walls may be curved, sloped, or convex. In addition, an occluder may include hole 80*h* for passage of shaft 31 or any portion of a manipulator.

Figure 20A:
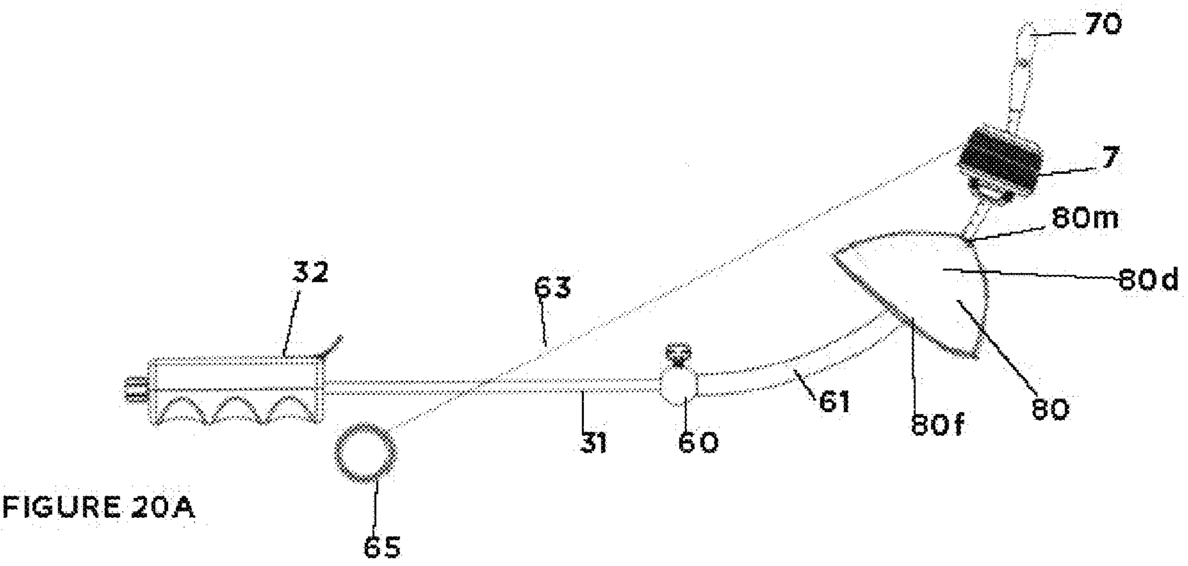
FIG. 20A illustrates an embodiment of a uterine manipulator with an occluder at the distal end of the outer tube.

FIG. 20A illustrates an embodiment of a uterine manipulator wherein the occluder is integrated with the distal end of outer tube 61 and substitutes distal ball 88. In this embodiment the occluder has a mushroom cap configuration with a domed outer surface 80*d* extending from circumference 80*f* to distal point 80*m*. The inner surface 80*i* may follow the shape of the outer surface 80*d*. In other embodiments, the inner surface 80*i* may be comprised of a plane perpendicular to the circumference (so the space between the circumference 80*f* and distal point 80*m* on the interior or inner surface of the occluder is filled with material).

In other embodiments with a distal ball 88, the occluder 80 may be positioned distal to distal ball 88 and give the appearance of one unit, though it is slideable along the shaft between the fornix delineator 7 and distal ball 88.

Figure 20B:
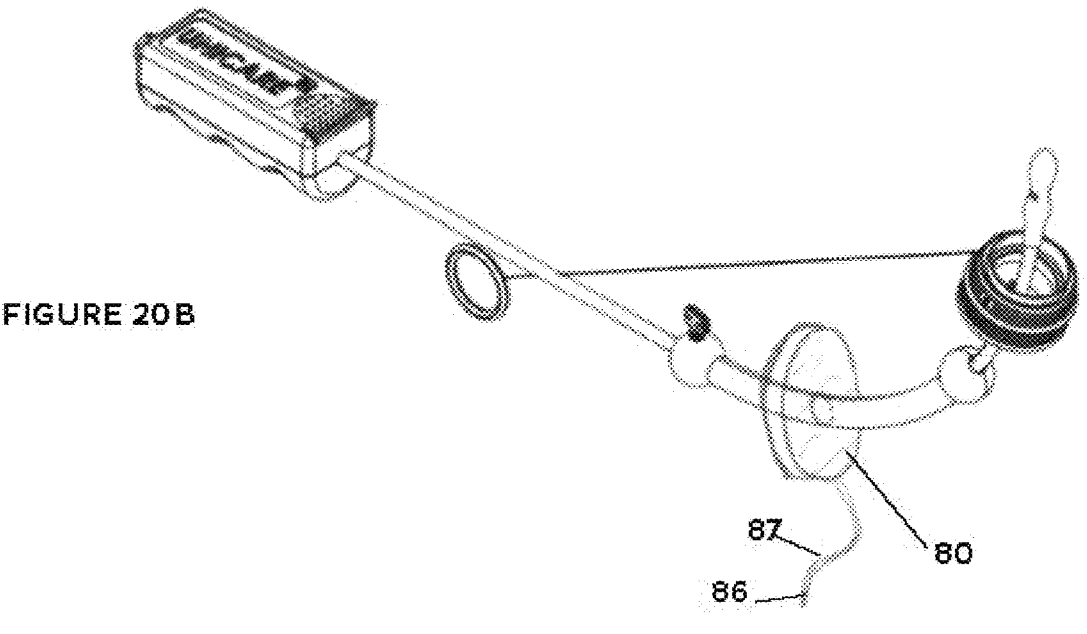
FIG. 20B illustrates an embodiment of a uterine manipulator with a balloon occluder.

FIG. 20B illustrates an embodiment of a uterine manipulator wherein a balloon occluder 80 is configured for coupling to the outer tube. Once inserted into the patent, the lumen 87 and luer lock or inlet 86 may hang outside the vagina introitus, and enables the physical to inflate the balloon. In other embodiments the balloon may be positioned distal to the distal ball 88 or outer tube 61, proximal to the outer tube 61, between the fastener or locking portion 60 and outer tube 61, or proximal to the fastener or locking portion 60, depending on the length of the vaginal canal.

Figure 20C:
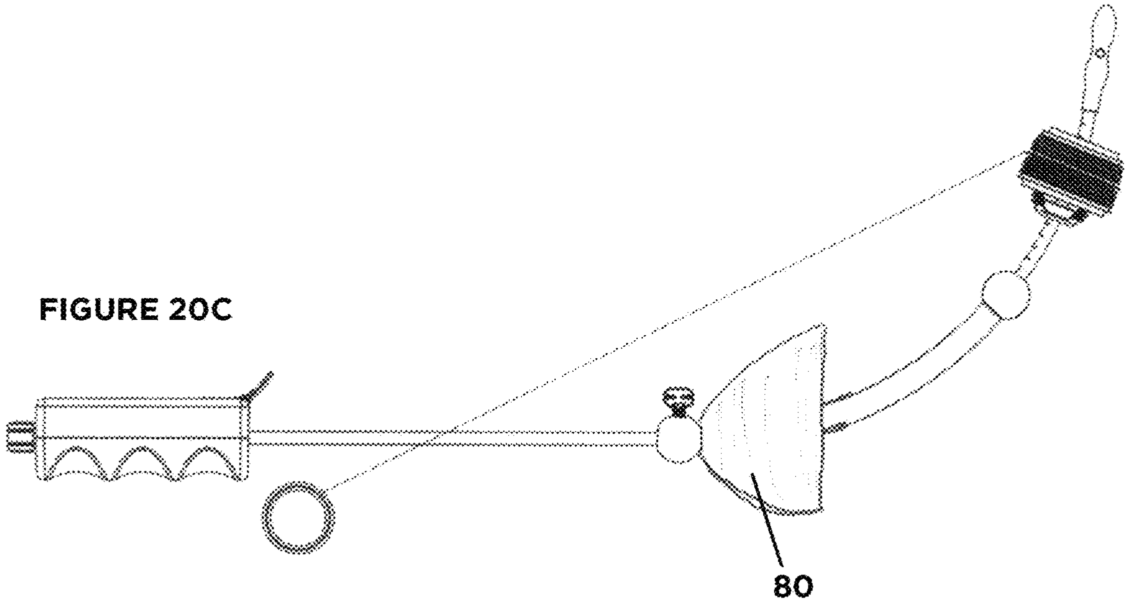
FIG. 20C illustrates an embodiment of a uterine manipulator with an occluder at the proximal end of the outer tube.

FIG. 20C illustrates an embodiment of a uterine manipulator including an occluder 80 coupled or integrated with a proximal portion of the outer tube, wherein the occluder has a mushroom cap configuration, like FIG. 20A. In this embodiment the narrow portion of the occluder is proximal, while the base portion is distal. In other embodiments, the occluder may be slidable along the outer tube, or slidable distal or proximal to the outer tube. This embodiment has the advantage of limiting leak of CO2.

Figure 20D:
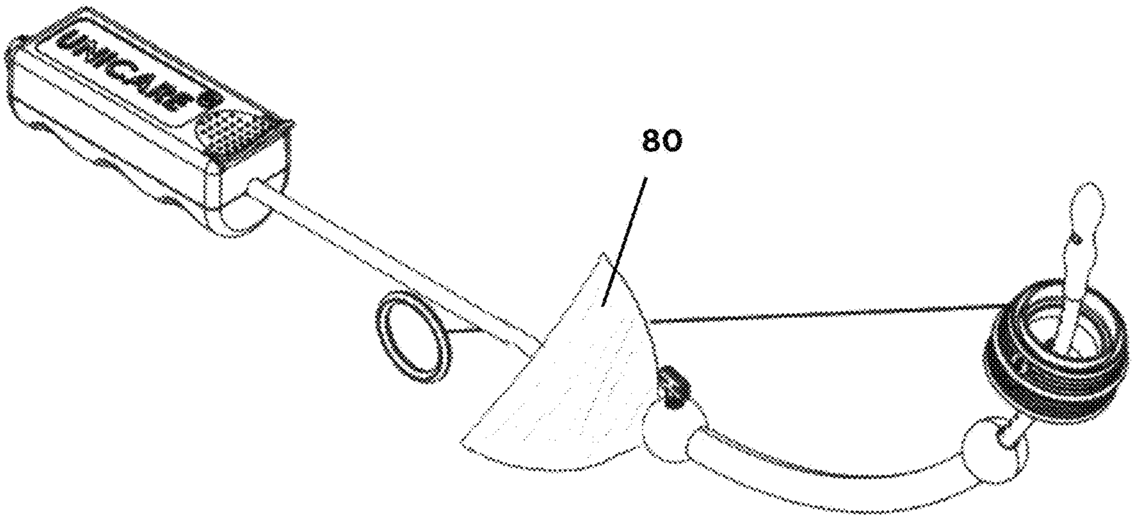
FIG. 20D illustrates an embodiment of a uterine manipulator with an occluder proximal to the fastener or locking portion of a uterine manipulator.

FIG. 20D illustrates an embodiment of a uterine manipulator including an occluder 80 positioned proximal to the fastener or locking portion 60, wherein the occluder has a mushroom cap configuration. In this embodiment the narrow portion of the occluder is distal, while the base portion is proximal. In embodiments, occluder may be slideable along the shaft 31. In other embodiments, the occluder may be coupled or integrated with the fastener or locking portion.

The embodiments of occluders 80 shown in FIGS. 20A-20D are merely illustrative. Any previously described or referenced occluder may substitute the occluders and may be comprised of alternative shapes and/or materials, and may partially or wholly coated or non-coated with non-porous, biocompatible material.

The following describes a series of possible steps associated with using an embodiment of the uterine manipulator with a Collar.

Pelvic Preparation:

a. Perform a pelvic exam in the lithotomy position, and estimate the size of the uterus and direction of the uterine fundus.
b. To ensure good visualization of the cervix, use a vaginal retractor (for example, a Sims Retractor) to access the cervix. Grasp the anterior or posterior lip of the cervix with tenaculum or Allis clamp.
c. Sound the uterine cavity to measure the sounding length from the external cervical os to the far end of the uterine cavity.
d. Dilate the cervical canal to Hegar Dilator No. 5 or a Pratt Dilator No. 15.
e. Apply a stitch using Zero Vicryl or a similar suture to the anterior cervical lip. Cut the short end of the stitch. Cut the long end of the stitch to 12 inches of length or more, and apply a clamp to the far end. Remove the needle. Repeat with posterior cervical lip.
f. Remove the tenaculum or Allis clamp and the vaginal retractor.

Collar Size Selection g. Remove the Manipulator from its sterile packaging and inspect for damage caused by shipping. Discard if any damage is noted.

h. Based on pelvic exam, select a Collar rim size that is appropriate for the patient's vaginal fornix and vaginal diameter.
i. Pass the cervical stitches through the Collar, making sure the selected Collar rim is facing the cervix.
j. Slide the Collar sideways (in its least traumatic orientation) into the vaginal canal, rotate 90 degrees within the vaginal canal, and press and fit the selected Collar rim against the vaginal fornix and around the cervix. Ensure Collar's Ring remains outside of the vagina.
k. If the Collar does not slide into vaginal canal easily or does not fit correctly against the vaginal fornix and around the cervix, then remove the Collar by pulling the Collar's Ring and repeat step B(1).

Insertion of Manipulator into the Uterine Cavity:

l. Advance the Outer Tube on the shaft until the Stabilizer's rim is at the sounding length of the uterus. (The graduations on the shaft are provided as a guide for comparison to a graduated uterine sound).
m. Unlock the Thumbscrew to Advance the Ball or Lock Body against the Outer Tube.
n. With the Thumbscrew pointing down on the posterior side of the device, turn the Thumbscrew clockwise to lock the Ball or Lock Body against the Outer Tube.
o. Remove the clamps from the cervical stitches.
p. Pass one cervical stitch through one Stabilizer window, and pass the other cervical stitch through the other stabilizer window. Re-secure each stitch's far end with a clamp.
q. Use a vaginal retractor (for example, a Sims Retractor) to access the cervix and surrounding Collar.
r. Pull the stitches to hold the cervix in place and advance the Manipulator through the cervical os into the uterine cavity in the direction of the uterine fundus until the Stabilizer is applied firmly against the Collar. If the uterus is anteverted, advance the Manipulator into the cervical os with the tip pointing up. If the uterus is retroverted, rotate the Manipulator 180° prior to insertion so the tip is pointing down, insert the Manipulator, and once inserted rotate the Manipulator back 180 degrees to antevert the uterus.
s. Remove the vaginal retractor.
t. Confirm the Thumbscrew is pointing down and on the posterior side of the Manipulator.
u. Pull the stitches taught and tie around the Thumbscrew's grooves.
v. Apply gentle traction to the Manipulator to ensure that the Manipulator is secure.

Various examples of embodiments are now discussed.

Example A-1 includes a uterine manipulator system comprising (1) a shaft wherein the shaft contains a hollow inner channel coupling a distal end of the shaft to a proximal end of the shaft; and wherein the distal end of the shaft includes at least one of a distal shaft aperture in fluid communication with the hollow inner channel, and the proximal end of the shaft includes at least one of a proximal shaft aperture in fluid communication with the hollow inner channel; (2) a handle at the proximal end of the shaft; wherein the handle includes a handle aperture at the proximal end of the shaft configured to couple to a fluid inlet; wherein the fluid inlet is in fluid communication with the proximal shaft aperture; (3) a tip having a maximum bulbous diameter greater than a maximum diameter of the shaft; wherein at least one or more of an aperture is located on the tip and is in fluid communication with the distal shaft aperture and the hollow inner channel; (3) an outer tube with a proximal end and a distal end wherein the outer tube is hollow with an inner diameter greater than the diameter of the shaft; wherein the outer tube is configured to slide between the proximal end of the shaft and the bulbous portion (4) a fastener positioned proximal to the outer tube's proximal end, wherein the fastener includes a (i) longitudinal hollow channel extending longitudinally through the fastener, wherein the longitudinal hollow channel is configured receive the shaft; (ii) a first vertical hollow channel extending from a top portion of the fastener to the longitudinal hollow channel, such that the longitudinal hollow channel and first vertical hollow channel are in fluid communication; (iii) a threaded portion on a first surface of the first vertical hollow channel (iv) a thumbscrew having a (i) screw head having one or more crevices, wherein the crevice is V, U or W shaped and (ii) a threaded vertical portion configured to screw into the first vertical hollow channel and couple to the shaft, thereby preventing motion of the outer tube towards the proximal end of the shaft.

In Example A2, the subject matter of Example A1 can optionally include the screw-head having one or more crevices, wherein the crevice is V shaped and less than 15 degrees.

In Example A3, the subject matter of Examples A1-2 can optionally include the fastener being coupled to the proximal portion of the outer tube.

In Example A4, the subject matter of Examples A1-3 can optionally include the fastener being a ball.

In Example A5, the subject matter of Examples A1-4 can optionally include the fastener further comprised of (i) a second vertical hollow channel extending vertically from a bottom portion of the fastener to the longitudinal hollow channel, such that the longitudinal hollow channel and second vertical hollow channel are in fluid communication; (ii) a threaded portion on a second surface of the second vertical hollow channel; and (iii) a second thumbscrew having a (i) screw head with one or more crevices wherein the crevice is V, U, or W shaped and (ii) a threaded vertical portion configured to screw into the fastener's second vertical hollow channel.

In Example A6, the subject matter of Examples A1-5 can optionally include the outer tube having a distal ball on the distal portion.

In Example A7, the subject matter of Examples A1-6 can optionally include the shaft comprised of a proximal portion, middle portion, and a distal portion; wherein the proximal and middle portion are straight, and the distal portion is curved to form a J configuration.

In Example A8, the subject matter of Examples A1-6 can optionally include the shaft comprised of a proximal portion, middle portion, and a distal portion; wherein the middle is a straight longitudinal portion, and the distal portion is curved to form a configuration, and the proximal portion forms an angle of less than 90 degrees to the straight longitudinal portion, such that the proximal portion and distal portion are positioned cis with respect to one another.

In Example A9, the subject matter of Examples A1-5 can optionally include the tip configured as a balloon.

In Example A10, the subject matter of Examples A1-5 can optionally include a tip 70 having an opening at a proximal first end; a closed end at a distal second end; a first proximal half, and a second distal half; a hollow channel extending between the first end and a second end; and a proximal hump on the first proximal half with a first diameter extending radially from the tip.

In Example A11, the subject matter of Examples A10 can optionally include the tip including one or more rings extending radially around the tip.

In Example A12, the subject matter of Examples A10-11 can optionally include the tip including one or more apertures.

In Example A13, the subject matter of Examples 1-5 can optionally include (1) a tip 70 having an opening at a proximal first end; a closed end at a distal second end; a first proximal half, and a second distal half; a hollow channel extending between the first end and a second end; and a distal hump with a first diameter extending radially from the tip on the distal half.

In Example A14, the subject matter of Examples A13 can optionally include the tip having a proximal hump with a second diameter extending radially from the tip.

In Example A15, the subject matter of Examples A14 can optionally include first diameter and the second diameter being equal.

In Example A16, the subject matter of Examples A14 can optionally include the first diameter being greater than the second diameter.

In Example A17, the subject matter of Examples A14 can optionally include the second diameter being greater than the first diameter.

In Example A18, the subject matter of Examples A14-17 can optionally include the tip including one or more rings extending radially around the tip.

In Example A19, the subject matter of Examples A1-18 can optionally include a flexible occluder having a hole having a diameter greater than a diameter of the shaft.

In Example A20, the subject matter of Examples A19 can optionally include the occluder comprised of a balloon with a lumen and an inlet or leer lock configured for receiving gas, wherein the balloon is a donut shape.

In Example A21, the subject natter of Examples A19 can optionally include the occluder being a sponge or a foam.

In Example A22, the subject matter of Examples A19-21 can optionally include the occluder being coated by a less porous biocompatible material.

In Example A23, the subject matter of Examples A19-22 can optionally include the occluder being in the shape of a disk with a first surface and a second surface.

In Example A24, the subject matter of Examples A19-23 can optionally include the occluder including crevices shaped as one a V, W, or U shape.

In Example A25, the subject matter of Examples A19-22 can optionally include the occluder having a domed outer surface.

In Example A26, the subject matter of Examples A19-25 can optionally include the occluder being coupled to the outer tube.

In Example A27, the subject matter of Examples A19-25 can optionally include the occluder being proximal to the outer tube.

In Example A28, the subject matter of Examples A19-25 can optionally include the occluder being distal to the outer tube.

In Example A29, the subject matter of Examples A19-25 can optionally include the occluder coupled to the fastener.

In Example A30, the subject matter of Examples A19-25 can optionally include occluder being slideable along the shaft.

In Example A31, the subject matter of Examples A19-30 can optionally include the occluder being removable.

Example B-1 includes a uterine manipulator system comprising: (1) a shaft wherein the shaft contains a hollow inner channel coupling a distal end of the shaft to a proximal end of the shaft; and wherein the distal end of the shaft includes at least one of a distal shaft aperture in fluid communication with the hollow inner channel, and the proximal end of the shaft includes at least one of a proximal shaft aperture in fluid communication with the hollow inner channel; (2) a handle at the proximal end of the shaft; wherein the handle includes a handle aperture at the proximal end of the shaft configured to couple to a fluid inlet; wherein the fluid inlet is in fluid communication with the proximal shaft aperture; (3) a tip having a maximum bulbous diameter greater than a maximum diameter of the shaft; wherein at least one or more of an aperture is located on the tip and is in fluid communication with the distal shaft aperture and the hollow inner channel; (4) an outer tube with a proximal end and a distal end wherein the outer tube is hollow with an inner diameter greater than the diameter of the shaft; wherein the outer tube is configured to slide between the proximal end of the shaft and the bulbous portion (5) a fastener positioned proximal to the outer tube's proximal end, wherein the fastener is a cap having (i) a proximal end with a proximal opening and first diameter, (ii) a distal end with a distal opening and a second diameter, (iii) a hollow inner cavity with an inner surface between the caps' proximal end and cap's distal end, and (iv) an outer surface between the proximal and distal end; wherein the proximal opening's first diameter is larger than a diameter of the shaft; distal opening's second diameter is larger than a diameter of the outer tube; wherein the distal opening is configured to couple or slide over the outer tube so that the outer tube is immobilized on the shaft.

In Example B-2, the subject matter of Examples B1 can optionally include (i) an outer surface of the outer tube's proximal end including first threads and (ii) a portion of the cap's inner surface including corresponding second threads to facilitate coupling of the outer tube and the cap via a screw mechanism.

In Example B-3, the subject matter of Examples B1-2 can optionally include the outer tube having one or more crevices and wherein the crevice(s) V, U, or W shaped.

In Example B-4, the subject matter of Examples B1-3 can optionally include the outer tube's diameter being reduced after coupling.

In Example B-5, the subject matter of Examples B1-4 can optionally include a portion of the outer tube's proximal end being in contact with the shaft after coupling.

In Example B-6 the subject matter of Examples B1-5 can optionally include the cap's inner surface being convex.

In Example B-7, the subject matter of Examples B1-6 can optionally include a layer of flexible, biocompatible material being in between the inner surface and outer surface.

In Example B-8, the subject matter of Examples B1-7 can optionally include the material being foam or sponge.

In Example B-9, the subject matter of Examples B1-7 can optionally include the material being a balloon, and a lumen with an inlet or leer lock are coupled to the balloon to facilitate inflation.

In Example B-10, the subject matter of Examples B1-9 can optionally include the cap's outer surface having one or more slits or crevices.

In Example B-11, the subject matter of Examples B1-10 can optionally include a portion of the outer surface being coated in a non-porous, biocompatible material.

In Example B-12, the subject matter of Examples B1-11 can optionally include the hollow inner cavity being a rigid material, such as plastic configured with threads.

In Example B-13, the subject matter of Examples B1-12 can optionally include the cap's proximal opening coupling to the outer tube's proximal end; the proximal opening's first diameter being less then the distal earning's second diameter; and wherein the cap's distal end is positioned distal to the outer tube's proximal end.

In Example B-14, the subject matter of Examples B1-12 can optionally include the cap's distal opening coupling to the outer tube's proximal end; the distal opening's second diameter bring less then the cap's proximal opening's first diameter; and wherein the cap's proximal end is positioned proximal to the outer tube's proximal end.

In Example B-15, the subject matter of Examples B1-12 can optionally include the cap's distal opening coupling to the outer tube's proximal end; the proximal opening's first diameter being less then the distal opening's second diameter; and wherein the cap's proximal end is positioned proximal to the outer tube's proximal end.

In Example B16, the subject matter of Examples B1-15 can optionally include the outer tube having a distal ball on the distal portion.

In Example B17, the subject matter of Examples B1-16 can optionally include the shaft comprised of a proximal portion, middle portion, and a distal portion; wherein the proximal and middle portion are straight, and the distal portion is curved to form a J configuration.

In Example B18, the subject matter of Examples B1-16 can optionally include the shaft comprised of a proximal portion, middle portion, and a distal portion; wherein the middle is a straight longitudinal portion, and the distal portion is curved to form a J configuration, and the proximal portion forms an angle of less than 90 degrees to the straight longitudinal portion, such that the proximal portion and distal portion are positioned cis with respect to one another.

In Example B19, the subject matter of Examples B1-18 can optionally include the tip configured as a balloon.

In Example B20, the subject matter of Examples B1-18 can optionally include a tip 70 having an opening at a proximal first end; a closed end at a distal second end; a first proximal half, and a second distal half, a hollow channel extending between the first end and a second end; and a proximal hump on the first proximal half with a first diameter extending radially from the tip.

In Example B21, the subject matter of Examples B20 can optionally include the tip including one or more rings extending radially around the tip.

In Example B22, the subject matter of Examples B20-21 can optionally include the tip including one or more apertures.

In Example B23, the subject matter of Examples B1-18 can optionally include (1) a tip 70 having an opening at a proximal first end; a closed end at a distal second end; a first proximal half, and a second distal half; a hollow channel extending between the first end and a second end; and a distal hump with a first diameter extending radially from the tip on the distal half.

In Example B24, the subject matter of Examples B23 can optionally include the tip having a proximal hump with a second diameter extending radially from the tip.

In Example B25, the subject matter of Examples B24 can optionally include first diameter and the second diameter being equal.

In Example B26, the subject matter of Examples B24 can optionally include the first diameter being greater than the second diameter.

In Example B27, the subject matter of Examples B24 can optionally include the second diameter being greater than the first diameter.

In Example B28, the subject matter of Examples B24-B27 can optionally include the tip including one or more rings extending radially around the tip.

In Example B29, the subject matter of Examples B1-B8 can optionally include a flexible occluder having a hole having a diameter greater than a diameter of the shaft.

In Example B30, the subject matter of Example B2.9 can optionally include the occluder comprised of a balloon with a lumen and an inlet or leer lock configured for receiving gas, wherein the balloon is a donut shape.

In Example B31, the subject matter of Example B29 can optionally include the occluder being a sponge or a foam.

In Example B32, the subject matter of Examples B29-31 can optionally include the occluder being coated by a less porous biocompatible material.

In Example B33, the subject matter of Examples B29-32 can optionally include the occluder being in the shape of a disk with a first surface and a second surface.

In Example B34, the subject matter of Examples B29-33 can optionally include the occluder including crevices shaped as one a V, W, or U shape.

In Example B35, the subject matter of Examples B29-32 can optionally include the occluder having a domed outer surface.

In Example B36, the subject matter of Examples B29-35 can optionally include the occluder being coupled to the outer tube.

In Example B37, the subject matter of Examples B29-35 can optionally include the occluder being proximal to the outer tube In Example B38, the subject matter of Examples B29-35 can optionally include the occluder being distal to the outer tube In Example B39, the subject matter of Examples B29-35 can optionally include the occluder coupled to the fastener.

In Example B40, the subject matter of Examples B29-35 can optionally include occluder being slideable along the shaft.

In Example B41, the subject matter of pies B29-40 can optionally include the occluder being removable.

Example C1 includes a fornix delineator configured to define the vaginal fornices and/or surround the cervix, comprised of (i) a first end with a first opening having a first diameter, surrounded by a first rim adapted to contact and define a vaginal fornices or surround a cervix; (ii) a second end, opposite the first end, with a second opening and a second diameter adapted to receive a shaft or a tip; wherein the first opening and second opening are round or circular; (iii) a third portion consisting coupling the first end to the second end with an inner surface adapted to contact a cervix and an outer surface adapted to contact a vaginal wall; wherein the first end, second end, and third portion define an inner cavity configured to receive a cervix; (iv) a string with a first end and second end and a weight, wherein the string's first end is coupled to the fornix delineator and the string's second end is coupled to the weight.

In Example C2, the subject matter of Examples C1 can optionally include the weight being a ring.

In Example C3, the subject matter of Examples C1-2 can optionally include the fornix delineator including an eyelet, and string's first end being coupled to the eyelet.

In Example C4, the subject matter of Examples C1-3 can optionally include the third portion including one or more raised ridges that protrude beyond the outer surface.

In Example C5, the subject matter of Examples C1-4 can optionally include the ridge being positioned at the midline of the third portion.

In Example C6, the subject matter of Examples C1-4 can optionally include a fornix delineator configured to couple to a uterine manipulator comprised of a: (1) a shaft wherein the shaft contains a hollow inner channel coupling a distal end of the shaft to a proximal end of the shaft; and wherein the distal end of the shaft includes at least one of a distal shaft aperture in fluid communication with the hollow inner channel, and the proximal end of the shaft includes at least one of a proximal shaft aperture in fluid communication with the hollow inner channel; (2) a handle at the proximal end of the shaft; wherein the handle includes a handle aperture at the proximal end of the shaft configured to couple to a fluid inlet; wherein the fluid inlet is in fluid communication with the proximal shaft aperture; (3) a tip having a maximum bulbous diameter greater than a maximum diameter of the shaft; wherein at least one or more of an aperture is located on the tip and is in fluid communication with the distal shaft aperture and the hollow inner channel; (3) an outer tube with a proximal end and a distal end wherein the outer tube is hollow with an inner diameter greater than the diameter of the shaft; wherein the outer tube is configured to slide between the proximal end of the shaft and the bulbous portion; wherein the fornix delineator is positioned distal to the outer tube.

In Example C7, the subject matter of Examples C1-6 can optionally include the outer tube having a distal ball on the distal portion.

In Example C8, the subject matter of Examples C-7 can optionally include the shaft comprised of a proximal portion, middle portion, and a distal portion; wherein the proximal and middle portion are straight, and the distal portion is curved to form a J configuration.

In Example C9, the subject matter of Examples C1-7 can optionally include the shaft comprised of a proximal portion, middle portion, and a distal portion; wherein the middle is a straight longitudinal portion, and the distal portion is curved to form a J configuration, and the proximal portion forms an angle of less than 90 degrees to the straight longitudinal portion, such that the proximal portion and distal portion are positioned cis with respect to one another.

In Example C10, the subject natter of Examples C1-9 can optionally include the tip configured as a balloon.

In Example C11, the subject matter of Examples C1-9 can optionally include a tip 70 having an opening at a proximal first end; a closed end at a distal second end; a first proximal half, and a second distal half; a hollow channel extending between the first end and a second end; and a proximal hump on the first proximal half with a first diameter extending radially from the tip.

In Example C12, the subject matter of Examples C11 can optionally include the tip including one or more rings extending radially around the tip.

In Example C13, the subject matter of Examples C11-12 can optionally include the tip including one or more apertures.

In Example C14, the subject matter of Examples C1-9 can optionally include (I) a tip 70 having an opening at a proximal first end; a closed end at a distal second end; a first proximal half, and a second distal half; a hollow channel extending between the first end and a second end; and a distal hump with a first diameter extending radially from the tip on the distal half.

In Example C15, the subject matter of Examples C14 can optionally include the tip having a proximal hump with a second diameter extending radially from the tip.

In Example C16, the subject matter of Examples C15 can optionally include first diameter and the second diameter being equal.

In Example C17, the subject matter of Examples C15 can optionally include the first diameter being greater than the second diameter.

In Example C18, the subject matter of Examples C15 can optionally include the second diameter being greater than the first diameter.

In Example C19, the subject matter of Examples C14-C18 can optionally include the tip including one or more rings extending radially around the tip.

In Example C20, the subject matter of Examples C1-C19 can optionally include a flexible occluder having a hole having a diameter greater than a diameter of the shaft.

In Example C21, the subject matter of Example C20 can optionally include the occluder comprised of a balloon with a lumen and an inlet or luer lock configured for receiving gas, wherein the balloon is a donut shape.

In Example C22, the subject matter of Example C20 can optionally include the occluder being a sponge or a foam.

In Example C23, the subject matter of Examples C20-22 can optionally include the occluder being coated by a less porous biocompatible material.

In Example C24, the subject matter of Examples C20-23 can optionally include the occluder being in the shape of a disk with a first surface and a second surface.

In Example C25, the subject matter of Examples C20-24 can optionally include the occluder including crevices shaped as one a V, W, or U shape.

In Example C26, the subject matter of Examples C20-25 can optionally include the occluder having a domed outer surface.

In Example C27, the subject matter of Examples C20-26 can optionally include the occluder being coupled to the outer tube.

In Example C28, the subject matter of Examples C20-26 can optionally include the occluder being proximal to the outer tube In Example C29, the subject matter of Examples C20-26 can optionally include the occluder being distal to the outer tube In Example C30, the subject matter of Examples C20-26 can optionally include the occluder coupled to the fastener.

In Example C31, the subject matter of Examples C20-26 can optionally include occluder being slideable along the shaft.

In Example C32, the subject matter of Examples C20-26 can optionally include the occluder being removable.

Example D1 includes a fornix delineator comprised of a (i) collar including (a)(i) a first end comprising a first opening, having a first diameter, surrounded by a first rim, (a)(ii) a second end, opposite the first end, having a second opening, having a second diameter that is larger than the first diameter, surrounded by a second rim, (a)(iii) an inner surface, coupling the first end to the second end, adapted to contact a cervix, (a)(iv) an outer surface adapted to contact a vaginal wall, (a)(v) a hollow tunnel, including the inner surface, the first opening, and the second opening wherein the hollow tunnel is adapted to receive the cervix; (ii) a string with a first end and second end; and (iii) a weight, wherein the string's first end is coupled to the collar and the string's second end is coupled to the weight.

In Example D2, the slab of Examples D1 can optionally include the weight being a ring.

In Example D3, the subject matter of Examples D1-2 can optionally e collar including an eyelet, and string's first end being coupled to the eyelet.

In Example D4, the subject matter of Examples D1-3 can optionally the collar including one or more raised ridges that protrude beyond the outer surface.

In Example D5, the subject matter of Examples D4 can optionally include the ridge being positioned at the midpoint between the first rim and the second.

In Example D6, the subject matter of Examples D1-D5 can optionally include a first size marking positioned between the collar first rim and ridge, and s second size marking positioned between the collar second rim and ridge.

In Example D7, the subject matter of Examples D1-6 can optionally include the outer tube having a distal ball on the distal portion.

In Example D8, the subject matter of Examples D1-7 can optionally include the shaft comprised of a proximal portion, middle portion, and a distal portion; wherein the proximal and middle portion are straight, and the distal portion is curved to form a J configuration.

In Example D9, the subject matter of Examples D1-7 can optionally include the shaft comprised of a proximal portion, middle portion, and a distal portion; wherein the middle is a straight longitudinal portion, and the distal portion is curved to form a J configuration, and the proximal portion forms an angle of less than 90 degrees to the straight longitudinal portion, such that the proximal portion and distal portion are positioned cis with respect to one another.

In Example D10 the subject matter of Examples D1-9 can optionally include the tip configured as a balloon.

In Example D11, the subject matter of Examples D1-9 can optionally include a tip 70 having an opening at a proximal first end; a closed end at a distal second end; a first proximal half, and a second distal half; a hollow channel extending between the first end and a second end; and a proximal hump on the first proximal half with a first diameter extending radially from the tip.

In Example D12, the subject matter of Examples D11 can optionally include the tip including one or more rings extending radially around the tip.

In Example D13, the subject matter of Examples D11-12 can optionally include the tip including one or more apertures.

In Example D14, the subject matter of Examples D1-9 can optionally include (1) a tip 70 having an opening at a proximal first end; a closed end at a distal second end; a first proximal half, and a second distal half; a hollow channel extending between the first end and a second end; and a distal hump with a first diameter extending radially from the tip on the distal half.

In Example D15, the subject matter of Examples D14 can optionally include the tip having a proximal hump with a second diameter extending radially from the tip.

In Example D16, the subject matter of Examples D15 can optionally include first diameter and the second diameter being equal.

In Example D17, the subject matter of Examples D15 can optionally include the first diameter being greater than the second diameter.

In Example D18, the subject matter of Examples D15 can optionally include the second diameter being greater than the first diameter.

In Example D19, the subject matter of Examples D14-C18 can optionally include the tip including one or more rings extending radially around the tip.

In Example D20, the subject matter of Examples D1-C19 can optionally include a flexible occluder having a hole having a diameter greater than a diameter of the shaft.

In Example D21, the subject matter of Example D20 can optionally include the occluder comprised of a balloon with a lumen and an inlet or leer lock configured for receiving gas, wherein the balloon is a donut shape.

In Example D22, the subject matter of Example D20 can optionally include the occluder being a sponge or a foam.

In Example D23, the subject matter of Examples D20-22 can optionally include the occluder being coated by a less porous biocompatible material.

In Example D24, the subject matter of Examples D20-23 can optionally include the occluder being in the shape of a disk with a first surface and a second surface.

In Example D25, the subject matter of Examples D20-24 can optionally include the occluder including crevices shaped as one a V, W, or U shape.

In Example D26, the subject matter of Examples D20-25 can optionally include the occluder having a domed outer surface.

In Example D27, the subject matter of Examples D20-26 can optionally include the occluder being coupled to the outer tube.

In Example D28, the subject matter of Examples D20-26 can optionally include the occluder being proximal to the outer tube In Example D29, the subject matter of Examples D20-26 can optionally include the occluder being distal to the outer tube In Example D30, the subject matter of Examples D20-26 can optionally include the occluder coupled to the fastener.

In Example D31, the subject matter of Examples D20-26 can optionally include occluder being slideable along the shaft.

In Example D32, the subject matter of Examples D20-26 can optionally include the occluder being removable.

Example E1 includes a uterine manipulator system comprising: (1) a shaft wherein the shaft contains a hollow inner channel coupling a distal end of the shaft to a proximal end of the shaft; and wherein the distal end of the shaft includes at least one of a distal shaft aperture in fluid communication with the hollow inner channel, and the proximal end of the shaft includes at least one of a proximal shaft aperture in fluid communication with the hollow inner channel; (2) a handle at the proximal end of the shaft; wherein the handle includes a handle aperture at the proximal end of the shaft configured to couple to a fluid inlet; wherein the fluid inlet is in fluid communication with the proximal shaft aperture; (3) a tip having a maximum bulbous diameter greater than a maximum diameter of the shaft; wherein at least one or more of an aperture is located on the tip and is in fluid communication with the distal shaft aperture and the hollow inner channel; (3) an outer tube with a proximal end and a distal end wherein the outer tube is hollow with an inner diameter greater than the diameter of the shaft; wherein the outer tube is configured to slide between the proximal end of the shaft and the bulbous portion (4) a fastener positioned proximal to the outer tube's proximal end comprising a stop with a first portion that is flush or parallel to the outer sliding tube, and a second portion that is angled or perpendicular to the outer tube; wherein (i) the outer tube's proximal end includes a cutout to receive the fastener; wherein in a first position the second portion is not in contact with the shaft, wherein in a second position, the second position is in contact with the shaft.

In Example E2, the subject matter of Examples E1 may include a pin traversing through a distal portion of the stop's first portion and coupling to the outer tube; wherein the outer tube includes a first hold and a second hole to receive the pin.

In Example E3, the subject matter of Examples E1-2 may include stop including an ergonomic thumb portion.

In Example E4, the subject matter of Examples E1-3 may include the stop including one or more crevices that are one of a U, V, or W shape configured for securing a stitch or suture.

In addition various methods may be employed in utilizer a uterine manipulator including:

An example of a method F1 includes removing a cervical cup or collar designed to define vaginal fornices for colpotomy; coupling a first end of a string to a ring; coupling the second end of the string to the collar; grasping the ring; pulling the ring such that the string applies force to the collar; rotating the collar to an atraumatic orientation responsive to the force being applied to the collar; pulling the ring to remove the collar from a vaginal introits.

In Example F2, the subject matter of Examples F1 may include the atraumatic orientation being a minimal length of the collar exits at the vaginal introitus.

In Example F3, the subject matter of Examples F1-2 may include the atraumatic orientation being across a diameter of the collar.

In example F4, the subject matter of Examples F1-3 may include the first end of the string being positioned outside of the vaginal introits.

In example F5, the subject matter of Examples F1-4 may include the collar being rotated and pulled off the vaginal fornices.

An example of a method G-1 includes a method for securing a uterine manipulator, comprising: affixing a first end of a stitch on a cervix; inserting the uterine manipulator; coupling a first screw with first crevices into the uterine manipulator; wrapping portions of the stitch that are distal to the first end of the stitch within the first crevices within the first screw.

In Example G2, the subject matter of Examples G1 may include coupling a second screw with second crevices into the uterine manipulator, wherein the second screw is positioned on an opposite side of the uterine manipulator as the first screw.

In Example G3, the subject matter of Examples G1-2 may include wrapping the portions of the stitch that are distal to the first end of the stitch within the second crevices within the second screw.

In Example G4, the subject matter of Examples G1-3 may include the first screw and the second screw being configured to be independently rotated to vary to angular offset of the first crevices and the second crevices.

The invention claimed is:

1. A medical device configured to define the vaginal fornices and/or surround the cervix, comprised of a fornix delineator having (i) a first end with a first opening having a first diameter, surrounded by a first rim adapted to contact and define a vaginal fornices or surround a cervix;

(ii) a second end, opposite the first end, with a second opening and a second diameter adapted to receive a shaft or a tip; wherein the first opening and second opening are round or circular, wherein the first end and the second end are reversible ends adapted to receive a cervix;

(iii) a third portion coupling the first end to the second end with an inner surface adapted to contact a cervix and an outer surface adapted to contact a vaginal wall; wherein the first end, second end, and third portion define an inner cavity configured to receive a cervix;

(iv) a string with a first extremity and second extremity and a weight, wherein the first extremity is coupled to the fornix delineator on a first ridge positioned on a midway point between the first end and the second end and the second end is coupled to the weight.

2. A medical device of claim 1, wherein the weight is a ring.

3. A medical device of claim 1, wherein the third portion includes one or more raised ridges that protrude beyond the outer surface, the one or more ridges including the first ridge.

4. A medical device of claim 1 comprised of a shaft wherein the shaft contains a hollow inner channel coupling a distal end of the shaft to a proximal end of the shaft; and wherein the distal end of the shaft includes a distal shaft aperture in fluid communication with the hollow inner channel, and the proximal end of the shaft includes a proximal shaft aperture in fluid communication with the hollow inner channel.

5. A medical device of claim 4, comprised of a handle at the proximal end of the shaft;

wherein the handle includes a handle aperture at the proximal end of the shaft configured to couple to a fluid inlet;

wherein the fluid inlet is in fluid communication with the proximal shaft aperture.

6. A medical device of claim 4 comprised of a tip having a maximum bulbous diameter greater than a maximum diameter of the shaft;

wherein at least one or more aperture is located on the tip and is in fluid communication with the distal shaft aperture and the hollow inner channel.

7. A medical device of claim 6, wherein the tip is configured as a balloon.

8. A medical device of claim 4 comprised of an outer tube with a proximal end and a distal end wherein the outer tube is hollow with an inner diameter greater than the diameter of the shaft;

wherein the outer tube is configured to slide between the proximal end of the shaft and the distal end of the shaft;

wherein the fornix delineator is positioned distal to the outer tube.

9. A medical device of claim 8, wherein the outer tube has a distal ball on the distal portion.

10. A medical device of claim 4 including a flexible occluder having a hole having a diameter greater than a diameter of the shaft.

11. A medical device of claim 10, wherein the occluder is comprised of a balloon with a lumen and an inlet or luer lock configured for receiving gas, wherein the balloon is a donut shape.

12. A medical device of claim 10, wherein the occluder is a sponge or a foam.

13. A medical device of claim 10 wherein a portion of the occluder is coated by a biocompatible material.

14. A medical device of claim 8, including a flexible occluder having a hole having a diameter greater than a diameter of the shaft and wherein the occluder is coupled to the outer tube.

15. A medical device of claim 8 comprised of a fastener positioned proximal to the outer tube's proximal end, wherein the fastener includes a (i) longitudinal hollow channel extending longitudinally through the fastener, wherein the longitudinal hollow channel is configured to receive the shaft;

(ii) a first vertical hollow channel extending from a top portion of the fastener to the longitudinal hollow channel, such that the longitudinal hollow channel and first vertical hollow channel are in fluid communication;

(iii) a threaded portion on a first surface of the first vertical hollow channel (iv) a thumbscrew having a (i) screw head having one or more crevices, wherein the crevice is V, U or W shaped and (ii) a threaded vertical portion configured to screw into the first vertical hollow channel and couple to the shaft extending through the longitudinal hollow channel, thereby preventing motion of the outer tube towards the proximal end of the shaft.

16. A medical device of claim 15, wherein the (a) fastener is further comprised of (i) a second vertical hollow channel extending vertically from a bottom portion of the fastener to the longitudinal hollow channel, such that the longitudinal hollow channel and second vertical hollow channel are in fluid communication;

(ii) a threaded portion on a second surface of the second vertical hollow channel; and (iii) a second thumbscrew having a (i) screw head with one or more crevices wherein the crevice is V, U, or W shaped and (ii) a threaded vertical portion configured to screw into the fastener's second vertical hollow channel.

17. A medical device of claim 8, comprised of a fastener positioned proximal to the outer tube's proximal end, wherein the fastener is a cap having (i) a proximal end with a proximal opening and first diameter, (ii) a distal end with a distal opening and a second diameter, (iii) a hollow inner cavity with an inner surface between the caps' proximal end and cap's distal end, and (iv) an outer surface between the proximal and distal end;

wherein the proximal opening's first diameter is larger than a diameter of the shaft; distal opening's second diameter is larger than a diameter of the outer tube;

wherein the distal opening is configured to couple or slide over the outer tube so that the outer tube is immobilized on the shaft.

18. A medical device of claim 17, wherein (i) an outer surface of the outer tube's proximal end includes first threads and (ii) a portion of the cap's inner surface includes corresponding second threads to facilitate coupling of the outer tube and the cap via a screw mechanism.

19. A medical device of claim 8, wherein the outer tube has one or more crevices and wherein the crevice(s) are V, U, or W shaped.

* * * * *